(12) United States Patent
Pasquier et al.

(10) Patent No.: US 6,570,019 B2
(45) Date of Patent: May 27, 2003

(54) CATIONIC PYRROLO-PYRROL-DERIVATIVES, METHOD FOR PRODUCING THEM AND COLORANTS FOR KERATIN FIBERS, CONTAINING THESE COMPOUNDS

(75) Inventors: Cécile Pasquier, Marly (CH); Patrick Wyss, Cormérod (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 09/958,565

(22) PCT Filed: Jan. 25, 2001

(86) PCT No.: PCT/EP01/00784

§ 371 (c)(1),
(2), (4) Date: Oct. 10, 2001

(87) PCT Pub. No.: WO01/62759

PCT Pub. Date: Aug. 30, 2001

(65) Prior Publication Data

US 2003/0055268 A1 Mar. 20, 2003

(30) Foreign Application Priority Data

Feb. 25, 2000 (DE) .......................... 100 09 070

(51) Int. Cl.$^7$ .................. C07D 487/04; C09B 57/00
(52) U.S. Cl. .................. 546/276.7; 548/311.7; 548/414; 548/453; 8/405
(58) Field of Search .................. 546/276.7; 548/414, 548/453, 331.7; 8/405

(56) References Cited

U.S. PATENT DOCUMENTS 5,169,953 A   12/1992   Mizuguchi .................. 544/144

FOREIGN PATENT DOCUMENTS

| DE | 40 11 927 A  | 10/1990 |
| DE | 40 37 556 A  | 5/1991  |
| DE | 44 35 211 A1 | 4/1995  |
| EP | 0 953 343 A  | 11/1999 |

Primary Examiner—Joseph K. McKane
Assistant Examiner—Andrea D. Small
(74) Attorney, Agent, or Firm—Michael J. Striker

(57) ABSTRACT

The object of the present invention are diketopyrrolopyrroles of the general formula (I)

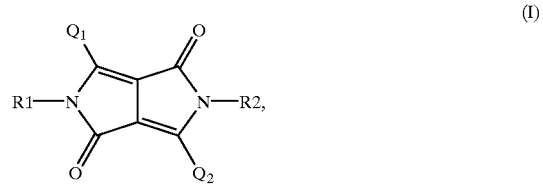

wherein, independently of one another, $Q_1$ and $Q_2$ represent an optionally substituted, aromatic, isocyclic or heterocyclic group with 5 to 14 atoms in the ring, the heterocyclic group containing at least one oxygen, nitrogen or sulfur atom, and the R1 and R2 groups, independently of one another represent hydrogen or a $Y-B^+A^-$ group, with the proviso that at least one of the R1 and R2 groups is not hydrogen; $B^+$ is an aromatic, aliphatic, alicyclic, aromatic heterocyclic or non-aromatic heterocyclic, quaternary ammonium group or a quaternary phosphonium group; Y is an optionally substituted linear or branched $C_1$ to $C_6$ alkylene group and $A^-$ is an anion; a method for their synthesis as well as agents, containing compounds of formula (I), for dyeing keratin fibers.

11 Claims, No Drawings

CATIONIC PYRROLO-PYRROL-DERIVATIVES, METHOD FOR PRODUCING THEM AND COLORANTS FOR KERATIN FIBERS, CONTAINING THESE COMPOUNDS

This application is a 371 of PCT/EP01/00784 Jan. 25, 2001.

BACKGROUND OF THE INVENTION

The object of the present invention are new cationic pyrrolopyrrole derivatives, a process for producing them and dyes, which are intended for keratin fibers and contain these compounds.

As a rule, two dyeing processes are used for treating keratin-containing fibers, such as human hair, wool or furs, for changing their color. In the first process, the dyeing is carried out with so-called oxidative or permanent dyes, using a mixture of different developing substances and coupling substances and an oxidizing agent. If necessary, for rounding off the dyeing result or for producing special color effects, so-called substantive (non-oxidative) dyes can be added. The second method exclusively uses substantive dyes, which are applied on the fibers in a suitable carrier composition. This method is easily employed, decidedly mild and distinguished by causing only little damage to the keratin fibers. The substantive dyes, used here, must meet a plurality of requirements. They must be safe toxicologically and dermatologically and make it possible to achieve dyeings in the desired intensity. Among other things, this also presupposes an adequate solubility in water. In addition, good light fastness, acid resistance and rubbing fastness for the dyeings achieved are required.

As a rule, a combination of different non-oxidative dyes is required for substantive (non-oxidative) dyes. Since the selection of red and blue dyes, which can be used in coloring agents for keratin fibers, is limited, there is furthermore a need for such dyes.

Water-soluble diketopyrrolo[3,4-c]pyrroles, which contain at least one water-solubilizing anionic group, are known from the German Offenlegungsschrift 40 11 927. These compounds are said to make uniform, brilliant dyeing of nitrogen-containing and cellulosic fibers possible with good fastness properties. Because of their inferior take-up properties on keratin fibers, such compounds usually give satisfactory dyeings only in conjunction with carriers. Furthermore, the EP publication 0 953 343 discloses the use of water-insoluble diketopyrrolo[3,4-c]pyrroles as dyeing pigments in cosmetic materials, such as makeup preparations. Likewise, the German Offenlegungsschrift 44 35 211 discloses dyketopyrroles, which are to find use as electrochrome materials in display systems.

SUMMARY OF THE INVENTION

It has now been found that, by introducing a cationic group, outstanding, water-soluble diketopyrrolo[3,4-c] pyrroles are obtained, which largely fulfill the aforementioned requirements and, without the addition of carriers, make intensive dyeings with good washing resistance, light stability and sweat resistance possible.

The object of the present invention therefore are, cationic diketopyrrolopyrroles of the general formula 1

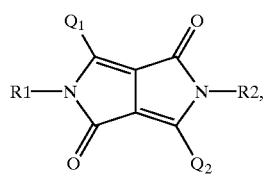

wherein, independently of one another, $Q_1$ and $Q_2$ represent an optionally substituted, aromatic, isocyclic or heterocyclic group with 5 to 14 atoms in the ring, the heterocyclic group containing at least one oxygen, nitrogen or sulfur atom, preferably an aromatic, monocyclic to tricyclic group, especially an aromatic, monocyclic or bicyclic group with 6 to 10 atoms, and the R1 and R2 groups, independently of one another represent hydrogen or a $Y-B^+A^-$ group, with the proviso that at least one of the R1 and R2 groups is not hydrogen; $B^+$ is an aromatic, aliphatic, alicyclic, aromatic heterocyclic or non-aromatic heterocyclic, quaternary ammonium group or a quaternary phosphonium group; Y is an optionally substituted, linear or branched $C_1$ to $C_6$ alkylene group and $A^-$ is an anion.

In the general formula (I) $B^+$ preferably represents (i) an aromatic, heterocyclic, quaternary ammonium compound, especially a quaternary compound of N-methylimidazole, N-allylimidazole, 2-ethylimidazole or 1,2-dimethylimidazole or a quaternary compound of pyridine, 4-dimethylaminopyridine, pyrimidine, pyrazole, N-methyl-pyrazole or quinoline; or (ii) a non-aromatic, heterocyclic, quaternary ammonium compound, especially a quaternary compound of diazabicyclo[2,2,2]octane, N-methyl-morpholine, N-ethylmorpholine, 1-methylpiperidine, or urotropine; or (iii) a quaternary, alkylammonium compound, arylammonium compound or arylakylammonium compound of the formula $NR^5R^6R^7$, in which $R^5$, $R^6$ and $R^7$ independently of one another represent a benzyl group, a phenyl group, or a $C_1$ to $C_6$ alkyl group, especially a methyl group, an ethyl group, a propyl group, an isopropyl group or a butyl group, the aforementioned alkyl group being unsubstituted or substituted with one or more hydroxy group or amino groups;

(iv) a quaternary phosphonium compound, especially a trialkylphosphonium compound or a triarylphosphonium compound. In particular, $B^+$ represents an N-methylimidazolium compound, a 4-dimethylaminopyridnium compound, a triethylammonium compound or a trimethylammonium compound.

In the general formula (I), Y preferably represents a $-CH_2-$ group, a $-CH_2-CH_2-$ group, a $-CH_2-CH_2-CH_2-$ group, $-CH_2-CH_2-CH_2-CH_2-$ group or a linear or branched $C_2$ to $C_6$ alkylene group, substituted with one or more alkyl groups, hydroxy groups, amino groups, acyl groups or quaternary ammonium groups, especially a substituted $-CH_2-CH_2-$ group, $-CH_2-CH_2-CH_2-$ group or $-CH_2-CH_2-CH_2-CH_2-$ group, such as a $-CH_2-CH(OH)-CH_2-$ group, the $-CH_2-CH_2-CH_2-CH_2-$ group being particularly preferred.

Especially preferred are compounds of formula (I), in which $Q_1$ and $Q_2$ independently of one another represent the following: phenyl, biphenyl, 3-pyridyl, 4-pyridyl, $C_6H_4R3$ or $C_6H_3R3R4$, in which R3 and R4 independently of one another are F, Cl, Br, I, CN, $NO_2$, $CF_3$, $C_1$ to $C_4$ alkyl, $C_1$ to $C_4$ alkoxy, aryloxy, $C_1$ to $C_4$ thioalkyl or NR'R", in which R' and R" independently of one another are hydrogen or a $C_1$ to $C_4$ alkyl group, or R'and R", together with the nitrogen atom, form an aromatic or aliphatic ring with 4 to 6 atoms, which optionally contains a further nitrogen, oxygen or sulfur atom.

Of the compounds of formula (I) named above, especially those are preferred, in which $Q_1$ and $Q_2$ independently of one another are phenyl, biphenyl, $C_6H_4R3$ or $C_6H_3R3R4$, in which R3 and R4 independently of one another are F, Cl, Br, CN, $C_1$ to $C_4$ alkyl, $C_1$ to $C_4$ alkoxy, $C_1$ to $C_4$ thioalkyl or NR'R", in which R' and R" independently of one another are hydrogen or a $C_1$ to $C_4$ alkyl group, or R' and R", together with the nitrogen atom, form an aromatic or aliphatic ring with 4 to 6 atoms, which optionally contains a further nitrogen, oxygen or sulfur atom.

In the general formula (I), $A^-$ preferably represents a chloride anion, a bromide anion or an iodide anion. It is, however, also possible to use, instead of a halide anion, other anions, which may be univalent as well as multivalent, such as a sulfate anion, a phosphate anion, a hydrogen phosphate anion, a carbonate anion, a bicarbonate anion, an oxalate anion, a formate anion, an acetate anion, a citrate anion, a tartrate anion, a malonate anion or a pyruvate anion, the number of anions, in the case of multivalent anions, having to be divided by the valence of the anion used. The bromide anion and the chloride anion are particularly preferred.

The following can be named as examples of suitable cationic diketo[pyrrolopyrroles of general formula (I): 2,5-bis-(4-trimethylammonium-butyl)-3,6-diphenyl-pyrrolo[3,4-c]pyrrole-1,4-dione dibromide; 2,5-bis(3-trimethyl-ammonium-propyl)-3,6-diphenyl-pyrrolo[3,4-c]pyrrole-1,4-dione dibromide; 2,5-bis(2-trimethylammonium-ethyl)-3,6-diphenyl-pyrrolo[3,4-c]-1,4-dione dibromide; 2,5-bis(2-trimethylammonium-butyl)-3,6-diphenyl-pyrrolo[3,4-c]pyrrole-1,4-dione dichloride; 2,5-bis(3-trimethylammonium-propyl)-3,6-diphenyl-pyrrolo[3,4-c]pyrrole-1,4-dione dichloride; 2,5-bis(2-trimethylammonium-ethyl)-3,6-diphenyl-pyrrolo-[3,4-c]pyrrole-1,4-dione dichloride; 2,5-bis[4-[4-(dimethylamino)-pyridinium]butyl]-3,6-diphenyl-pyrrolo[3,4-c]pyrrole-1,4-dione dibromide; 2,5-bis[3-[4-(dimethylamino)pyridinium]propyl]-3,6-diphenyl-pyrrolo[3,4-c]pyrrole-1,4-dione dibromide; 2,5-bis[2-[4-(dimethylamino)pyridinium]ethyl]-3,6-diphenyl-pyrrolo-[3,4-c]pyrrole-4-dione dibromide; 2,5-bis[4-[4-(dimethylamino)-pyridinium]butyl]-3,6-diphenyl-pyrrolo[3,4-c]-pyrrole-1,4-dione dichloride; 2,5-bis[3-[4-(dimethylamino)-pyridinium]propyl]-3,6-diphenyl-pyrrolo[3,4-c]pyrrole-1,4-dione dichloride; 2,5-bis[2-[4-(dimethylamino)pyridinium]ethyl]-3,6-diphenyl-pyrrolo-[3,4-c]pyrrole-1,4-dione dichloride; 2,5-bis(4-trimethylammonium-butyl)-3,6-bis(4-chlorophenyl)-pyrrolo[3,4-c]pyrrole-1,4-dione dibromide; 2,5-bis(3-trimethylammonium-propyl)-3,6-bis(4-chlorophenyl)-pyrrolo[3,4-c]pyrrole-1,4-dione dibromide; 2,5-bis(2-trimethylammonium-ethyl)-3,6-bis(4-chlorophenyl)-pyrrolo-[3,4-c]pyrrole-1,4-dione dibromide; 2,5-bis(4-trimethylammonium-butyl)-3,6-bis(4-chlorophenyl)-pyrrolo[3,4-c]pyrrole-1,4-dione dichloride; 2,5-bis(3-trimethylammonium-propyl)-3,6-bis(4-chlorophenyl)-pyrrolo[3,4-c]pyrrole-1,4-dione dichloride; 2,5-bis(2-trimethyl-ammonium-ethyl)-3,6-bis(4-chlorophenyl)-pyrrolo-[3,4-c]pyrrole-1,4-dione dichloride; 2,5-bis[4-[4-(dimethylamino)pyridinium]butyl]-3,6-bis(4-chlorophenyl)-pyrrolo[3,4-c]pyrrole-1,4-dione dibromide; 2,5-bis[3-[4-(dimethylamino)pyridinium]-propyl]-3,6-bis (4-chlorophenyl)-pyrrolo[3,4-c]pyrrole-1,4-dione dibromide; 2,5-bis[2-[4-(dimethylamino)pyridinium]ethyl]-3,6-bis(4-chlorophenyl)-pyrrolo[3,4-c]pyrrole-1,4-dione dibromide; 2,5-bis[4-[4-(dimethylamino)pyridinium]butyl]-3,6-bis(4-chlorophenyl)-pyrrolo[3,4-c]-pyrrole-1,4-dione dichloride; 2,5-bis[3-[4-(dimethylamino)pyridinium]propyl]-3,6-bis(4-chlorophenyl)-pyrrolo[3,4-c]pyrrole-1,4-dione dichloride; 2,5-bis[2-[4-(dimethylamino)pyridinium]ethyl]-3,6-bis(4-chlorophenyl)-pyrrolo[3,4-c]-pyrrole-1,4-dione dichloride; 2,5-bis(4-trimethyl-ammonium-butyl)-3,6-bis(4-t-butyl-phenyl)-pyrrolo[3,4-c]pyrrole-1,4-dione dibromide; 2,5-bis(3-trimethylammonium-propyl)-3,6-bis(4-t-butyl-phenyl)-pyrrolo[3,4-c]-pyrrole-1,4-dione dibromide; 2,5-bis(2-trimethylammonium-ethyl)-3,6-bis(4-t-butyl-phenyl)-pyrrolo-[3,4-c]pyrrole-1,4-dione dibromide; 2,5-bis(4-trimethylammonium-butyl)-3,6-bis(4-t-butyl-phenyl)-pyrrolo[3,4-c]pyrrole-1,4-dione dichloride; 2,5-bis(3-trimethylammonium-propyl)-3,6-bis(4-t-butyl-phenyl)-pyrrolo[3,4-c]pyrrole-1,4-dione dichloride; 2,5-bis(2-trimethylammonium-ethyl)-3,6-bis(4-t-butyl-phenyl)-pyrrolo[3,4-c]pyrrole-1,4-dione dichloride; 2,5-bis[4-[4-(dimethylamino)-pyridinium]butyl]-3,6-bis(4-t-butyl-phenyl)-pyrrolo[3,4-c]pyrrole-1,4-dione dibromide; 2,5-bis[3-[4-(dimethylamino)pyridinium]propyl]-3,6-bis(4-t-butyl-phenyl)-pyrrolo[3,4-c]pyrrole-1,4-dione dibromide; 2,5-bis[2-[4-(dimethyl-amino)-pyridinium]ethyl]-3,6-bis(4-t-butyl-phenyl)-pyrrolo-[3,4-c]pyrrole-1,4-dione dibromide; 2,5-bis[4-[4-(dimethylamino)pyridinium]butyl]-3,6-bis(4-t-butyl-phenyl)-pyrrolo[3,4-c]-pyrrole-1,4-dione dichloride; 2,5-bis[3-[4-(dimethylamino)-pyridinium]propyl]-3,6-bis(4-t-butyl-phenyl)-pyrrolo[3,4-c]pyrrole-1,4-dione dichloride; 2,5-bis[2-[4-(dimethylamino)pyridinium]ethyl]-3,6-bis(4-t-butyl-phenyl)-pyrrolo-[3,4-c]pyrrole-1,4-dione dichloride; 2,5-bis(4-trimethylammonium-butyl)-3,6-bis(biphenyl)-pyrrolo[3,4-c]pyrrole-1,4-dione-bromide; 2,5-bis(3-trimethyl-ammonium-propyl)-3,6-bis(biphenyl)-pyrrolo[3,4-c]pyrrole-1,4-dione dibromide; 2,5-bis(2-trimethylammonium-ethyl)-3,6-bis(biphenyl)-pyrrolo[3,4-c]pyrrole-1,4-dione dibromide; 2,5-bis(4-trimethylammonium-butyl)-3,6-bis(biphenyl)-pyrrolo[3,4-c]pyrrole-1,4-dione dichloride; 2,5-bis(3-trimethylammonium-propyl)-3,6-bis(biphenyl)-pyrrolo[3,4-c]pyrrole-1,4-dione dichloride; 2,5-bis(2-trimethyl-ammonium-ethyl)-3,6-bis(biphenyl)-pyrrolo[3,4-c]pyrrole-1,4-dione dichloride; 2,5-bis[4-[4-(dimethylamino)pyridinium]butyl]-3,6-bis(biphenyl)-pyrrolo[3,4-c]pyrrole-1,4-dione dibromide; 2,5-bis[3-[4-(dimethylamino)pyridinium]propyl]-3,6-bis(biphenyl)-pyrrolo[3,4-c]pyrrole-1,4-dione dibromide; 2,5-bis[2-[4-(dimethyl-amino)pyridinium]ethyl]-3,6-bis(biphenyl)-pyrrolo[3,4-c]pyrrole-1,4-dione dibromide; 2,5-bis[4-[4-(dimethylamino)pyridinium]butyl]-3,6-bis(biphenyl)-pyrrolo[3,4-c]-pyrrole-1,4-dione dichloride; 2,5-[3-[4-(dimethylamino)-pyridinium]-propyl]-3,6-bis(biphenyl)-pyrrolo[3,4-c]pyrrole-1,4-dione dichloride; 2,5-bis[2-[4-(dimethylamino)pyridinium]ethyl]-3,6-bis(biphenyl)-pyrrolo-[3,4-c]pyrrole-1,4-dione dichloride; 2,5-bis(4-trimethylammonium-butyl)-3,6-bis(3-chlorophenyl)-pyrrolo[3,4-c]pyrrole-1,4-dione dibromide; 2,5-bis(3-trimethylammonium-propyl)-3,6-bis(3-chlorophenyl)-pyrrolo[3,4-c]pyrrole-1,4-dione dibromide; 2,5-bis(2-trimethyl-ammonium-ethyl)-3,6-bis(3-chlorophenyl)-pyrrolo-[3,4-c]pyrrole-1,4-dione dibromide; 2,5-bis(4-trimethylammonium-butyl)-3,6-bis(3-chlorophenyl)-pyrrolo[3,4-c]pyrrole-1,4-dione dichloride; 2,5-bis(3-trimethylammonium-propyl)-3,6-bis(3-chlorophenyl)-pyrrolo[3,4-c]pyrrole-1,4-dione dichloride; 2,5-bis(2-trimethyl-ammonium-ethyl-3,6-bis(3- chlorophenyl)-pyrrolo-[3,4-c]pyrrole-1,4-dione dichloride; 2,5-bis[4-[4-(dimethylamino)pyridinium]butyl]-3,6-bis(3-chlorophenyl)-pyrrolo[3,4-c]pyrrole-1,4-dione dibromide; 2,5-bis[3-[4-(dimethylamino)-pyridinium]propyl]-3,6-bis(3-chlorophenyl)-pyrrolo[3,4-c]pyrrole-1,4-dione dibromide; 2,5-bis[2-[4-(dimethylamino)pyridinium]ethyl]-3,6-bis(3-chlorophenyl)-pyrrolo[3,4-c]pyrrole-1,4-dione dibromide; 2,5-bis[4-[4-(dimethylamino)-pyridinium]butyl]-3,6-bis(3-chlorophenyl)-pyrrolo[3,4-c]pyrrole-1,4-dione dichloride; 2,5-bis[3-[4-(dimethylamino)pyridinium]propyl]-3,6-bis(3-chlorophenyl)-pyrrolo[3,4-c]pyrrole-1,4-dione dichloride; 2,5-bis[2-[4-(dimethylamino)-pyridinium]ethyl]-3,6-bis(3-chlorophenyl)-pyrrolo[3,4-c]pyrrole-1,4-dione dichloride; 2,5-bis(4-trimethylammonium-butyl)-3,6-bis(4-methyl-phenyl)-pyrrolo[3,4-c]pyrrole-1,4-dione dibromide; 2,5-bis(3-trimethylammonium-propyl)-3,6-bis(4-methyl-phenyl)-pyrrolo[3,4-c]pyrrole-1,4-dione dibromide; 2,5-bis(2-trimethylammonium-ethyl)-3,6-bis(4-methyl-phenyl)-pyrrolo[3,4-c]pyrrole-1,4-dione dibromide; 2,5-bis(4-trimethylammonium-butyl)-3,6-bis(4-methyl-phenyl)-pyrrolo[3,4-c]pyrrole-1,4-dione dichloride; 2,5-bis(3-trimethylammonium-propyl)-3,6-bis(4-methyl-phenyl)-pyrrolo[3,4-c]pyrrole-1,4-dione dichloride; 2,5-bis(2-trimethylammonium-ethyl)-3,6-bis(4-methyl-phenyl)-pyrrolo[3,4-c]pyrrole-1,4-dione dichloride; 2,5-bis[4-[4-(dimethylamino)pyridinium]butyl]-3,6-bis(4-methyl-phenyl)-pyrrolo[3,4-c]pyrrole-1,4-dione dibromide; 2,5-bis[3-[4-(dimethylamino)-pyridinium]propyl]-3,6-bis(4-methyl-phenyl)-pyrrolo[3,4-c]pyrrole-1,4-dione dibromide; 2,5-bis[2-[4-(dimethylamino)pyridinium]ethyl]-3,6-bis(4-methyl-phenyl)-pyrrolo[3,4-c]pyrrole-1,4-dione dibromide; 2,5-bis[4-[4-(dimethylamino)-pyridinium]butyl]-3,6-bis(4-methyl-phenyl)-pyrrolo[3,4-c]pyrrole-1,4-dione dichloride; 2,5-bis[3-[4-(dimethyl-amino)pyridinium]propyl]-3,6-bis(4-methyl-phenyl)-pyrrolo[3,4-c]pyrrole-1,4-dichloride; 2,5-bis[2-[4-(dimethylamino)pyridinium]ethyl]-3,6-bis(4-methyl-phenyl)-pyrrolo[3,4-c]pyrrole-1,4-dione dichloride; 2,5-bis(4-trimethylammonium-butyl)-3,6-bis(3-methyl-phenyl)-pyrrolo[3,4-c]pyrrole-1,4-dione dibromide; 2,5-bis(3-trimethyl-ammonium-propyl)-3,6-bis(3-methyl-phenyl)-pyrrolo[3,4-c]pyrrole-1,4-dione dibromide; 2,5-bis(2-trimethylammonium-ethyl)-3,6-bis(3-methyl-phenyl)-pyrrolo[3,4-c]pyrrole-1,4-dione dibromide; 2,5-bis(4-trimethylammonium-butyl)-3,6-bis(3-methyl-phenyl)-pyrrolo[3,4-c]pyrrole-1,4-dione dichloride; 2,5-bis(3-trimethylammonium-propyl)-3,6-bis(3-methyl-phenyl)-pyrrolo[3,4-c]pyrrole-1,4-dione dichloride; 2,5-bis(2-trimethylammonium-ethyl)-3,6-bis(3-methyl-phenyl)-pyrrolo[3,4-c]pyrrole-1,4-dione dichloride; 2,5-bis[4-[4-(dimethylamino)-pyridinium]butyl]-3,6-bis(3-methyl-phenyl)-pyrrolo[3,4-c]pyrrole-1,4-dione dibromide; 2,5-bis[3-[4-(dimethylamino)-pyridinium]propyl]-3,6-bis(3-methyl-phenyl)-pyrrolo[3,4-c]pyrrole-1,4-dione dibromide; 2,5-bis[2-[4-(dimethylamino)-pyridinium]ethyl]-3,6-bis(3-methyl-phenyl)-pyrrolo[3,4-c]pyrrole-1,4-dione dibromide; 2,5-bis[4-[4-(dimethylamino)pyridinium]butyl]-3,6-bis(3-methyl-phenyl)-pyrrolo[3,4-c]pyrrole-1,4-dione dichloride; 2,5-bis[3-[4-(dimethylamino)-pyridinium]propyl]-3,6-bis(3-methyl-phenyl)-pyrrolo[3,4-c]pyrrole-1,4-dione dichloride; 2,5-bis[2-[4-(dimethylamino)pyridinium]ethyl]-3,6-bis(3-methyl-phenyl)-pyrrolo[3,4-c]pyrrole-1,4-dione dichloride; 2,5-bis(4-trimethylammonium-butyl)-3,6-bis(4-cyano-phenyl)-pyrrolo[3,4-c]pyrrole-1,4-dione dibromide; 2,5-bis(3-trimethylammonium-propyl)-3,6-bis(4-cyano-phenyl)-pyrrolo[3,4-c]pyrrole-1,4-dione dibromide; 2,5-bis(2-trimethylammonium-ethyl)-3,6-bis(4-cyano-phenyl)-pyrrolo[3,4-c]pyrrole-1,4-dione dibromide; 2,5-bis(4-trimethylammonium-butyl)-3,6-bis(4-cyano-phenyl)-pyrrolo[3,4-c]pyrrole-1,4-dione dichloride; 2,5-bis(3-trimethylammonium-propyl)-3,6-bis(4-cyano-phenyl)-pyrrolo[3,4-c]pyrrole-1,4-dione dichloride; 2,5-bis(2-trimethylammonium-ethyl)-3,6-bis(4-cyano-phenyl)-pyrrolo[3,4-c]pyrrole-1,4-dione dichloride; 2,5-bis[4-[4-(dimethylamino)pyridinium]-butyl]-3,6-(4-cyano-phenyl)-pyrrolo[3,4-c]pyrrole-1,4-dione dibromide; 2,5-bis[3-[4-(dimethylamino)-pyridinium]propyl]-3,6-bis(4-cyano-phenyl)-pyrrolo[3,4-c]pyrrole-1,4-dione dibromide; 2,5-bis[2-[4-(dimethylamino)pyridinium]ethyl]-3,6-bis(4-cyano-phenyl)-pyrrolo[3,4-c]pyrrole-1,4-dione dibromide; 2,5-bis[4-[4-(dimethyl-amino)pyridinium]butyl]-3,6-bis(4-cyano-phenyl)-pyrrolo[3,4-c]pyrrole-1,4-dione dichloride; 2,5-bis[3-[4-(dimethylamino)pyridinium]propyl]-3,6-bis(4-cyano-phenyl)-pyrrolo[3,4-c]pyrrole-1,4-dione dichloride; 2,5-bis[2-[4-(dimethylamino)pyridinium]-ethyl]-3,6-bis(4-cyano-phenyl)-pyrrolo[3,4-c]pyrrole-1,4-dione dichloride; 2,5-bis(4-trimethylammonium-butyl)-3,6-bis(3-cyano-phenyl)-pyrrolo[3,4-c]pyrrole-1,4-dione dibromide; 2,5-bis(3-trimethylammonium-propyl)-3,6-bis(3-cyano-phenyl)-pyrrolo[3,4-c]pyrrole-1,4-dione dibromide; 2,5-bis(2-trimethylammonium-ethyl)-3,6-bis(3-cyano-phenyl)-pyrrolo[3,4-c]pyrrole-1,4-dione dibromide; 2,5-bis(4-trimethylammonium-butyl)-3,6-bis(3-cyano-phenyl)-pyrrolo[3,4-c]pyrrole-1,4-dione dichloride; 2,5-bis(3-trimethylammonium-propyl)-3,6-bis(3-cyano-phenyl)-pyrrolo-[3,4-c]pyrrole-1,4-dione dichloride; 2,5-bis(2-trimethylammonium-ethyl)-3,6-bis(3-cyano-phenyl)-pyrrolo-[3,4-c]pyrrole-1,4-dione dichloride; 2,5-bis[4-[4-(dimethyl-amino)pyridinium]butyl]-3,6-bis(3-cyano-phenyl)-pyrrolo[3,4-c]pyrrole-1,4-dione dibromide; 2,5-bis[3-[4-(dimethylamino)-pyridinium]-propyl]-3,6-bis(3-cyano-phenyl)-pyrrolo[3,4-c]pyrrole-1,4-dione dibromide; 2,5-bis[2-[4-(dimethylamino)-pyridinium]ethyl]-3,6-bis(3-cyano-phenyl)-pyrrolo[3,4-c]pyrrole-1,4-dione dibromide; 2,5-bis[4-[4-(dimethylamino)-pyridinium]butyl]-3,6-bis(3-cyano-phenyl)-pyrrolo[3,4-c]pyrrole-1,4-dione dichloride; 2,5-bis[3-[4-(dimethylamino)pyridinium]-propyl]-3,6-bis(3-cyano-phenyl)-pyrrolo[3,4-c]pyrrole-1,4-dione dichloride; 2,5-bis[2-[4-(dimethylamino)pyridinium]ethyl]-3,6-bis(3-cyano-phenyl)-pyrrolo[3,4-c]pyrrole-1,4-dione dichloride; 2,5-bis(4-trimethylammonium-butyl)-3,6-bis(4-dimethylaminophenyl)-pyrrolo[3,4-c]pyrrole-1,4-dione dibromide; 2,5-bis(3-trimethylammonium-propyl)-3,6-bis(4-dimethylamino-phenyl)-pyrrolo[3,4-c]pyrrole-1,4-dione dibromide; 2,5-bis(2-trimethylammonium-ethyl)-3,6-bis(4-dimethylamino-phenyl)-pyrrolo[3,4-c]pyrrole-1,4-dione dibromide; 2,5-bis(4-trimethylammonium-butyl)-3,6-bis(4-dimethylamino-phenyl)-pyrrolo[3,4-c]pyrrole-1,4-dione dichloride; 2,5-bis(3-trimethylammonium-propyl)-3,6-bis(4-dimethylamino-phenyl)-pyrrolo[3,4-c]pyrrole-1,4-dione dichloride; 2,5-bis(2-trimethylammonium-ethyl)-3,6-bis(4-dimethylamino-phenyl)-pyrrolo[3,4-c]pyrrole-1,4-dione dichloride; 2,5-bis[4-[4-(dimethylamino)pyridinium]butyl]-3,6-bis(4-dimethylamino-phenyl)-pyrrolo[3,4-c]pyrrole-1,4-dione dibromide; 2,5-bis[3-[4-(dimethylamino)pyridinium]propyl]-3,6-bis(4-dimethylamino-phenyl)-pyrrolo[3,4-c]pyrrole-1,4-dione dibromide; 2,5-bis[2-[4-(dimethylamino)pyridinium]ethyl]-3,6-bis(4-dimethylamino-phenyl)-pyrrolo[3,4-c]pyrrole-1,4-dione dibromide; 2,5-bis[4-[4-(dimethylamino)pyridinium]butyl]-3,6-bis(4-dimethylamino-phenyl)-pyrrolo[3,4-c]pyrrole-1,4-dione dichloride; 2,5-bis[3-[4-(dimethylamino)pyridinium]propyl]-3,6-bis(4-dimethylamino-phenyl)-pyrrolo[3,4-c]pyrrole-1,4-dione dichloride; 2,5-bis[2-[4-(dimethylamino)pyridinium]ethyl]-3,6-bis(4- dimethylaminophenyl)-pyrrolo[3,4-c]pyrrole-1,4-dione dichloride; 2,5-bis[4-[N-(methylimidazolium)butyl]]-3,6-diphenyl-pyrrolo[3,4-c]pyrrole-1,4-dione dibromide; 2,5-bis[3-[N-(methylimidazolium)propyl]]-3,6-diphenyl-pyrrolo[3,4-c]pyrrole-1,4-dione dibromide; 2,5-bis[2-[N-(methylimidazolium)ethyl]]-3,6-diphenyl-pyrrolo-[3,4-c]pyrrole-1,4-dione dibromide; 2,5-bis[4-[N-(methylimidazolium)butyl]]-3,6-diphenyl-pyrrolo[3,4-c]pyrrole-1,4-dione dichloride; 2,5-bis[3-[N-(methylimidazolium)-propyl]]-3,6-diphenyl-pyrrolo[3,4-c]pyrrole-1,4-dione dichloride; 2,5-bis[2-[N-(methylimidazolium)ethyl]]-3,6-diphenyl-pyrrolo-[3,4-c]pyrrole-1,4-dione dichloride; 2,5-bis[4-[N-(methylimidazolium)butyl]]-3,6-bis(4-t-butyl-phenyl)-pyrrolo[3,4-c]pyrrole-1,4-dione dibromide; 2,5-bis[3-[N-(methylimidazolium)propyl]]-3,6-bis(4-t-butyl-phenyl)-pyrrolo-[3,4-c]pyrrole-1,4-dione dibromide; 2,5-bis[2-[N-(methylimidazolium)ethyl]]-3,6-bis(4-t-butyl-phenyl)-pyrrolo-[3,4-c]pyrrole-1,4-dione dibromide; 2,5-bis[4-[N-(methylimidazolium)-butyl]]-3,6-bis(4-t-butyl-phenyl)-pyrrolo[3,4-c]pyrrole-1,4-dione dichloride; 2,5-bis[3-[N-(methylimidazolium)-propyl]]-3,6-bis(4-t-butyl-phenyl)-pyrrolo[3,4-c]pyrrole-1,4-dione dichloride; 2,5-bis[2-[N-(methylimidazolium)ethyl]]-3,6-bis(4-t-butyl-phenyl)-pyrrolo[3,4-c]pyrrole-1,4-dione dichloride; 2,5-bis[4-[N-(methylimidazolium)butyl]]-3,6-bis(4-chlorophenyl)-pyrrolo[3,4-c]pyrrole-1,4-dione dibromide; 2,5-bis[3-[N-(methylimidazolium)propyl]]-3,6-bis(4-chlorophenyl)-pyrrolo-[3,4-c]pyrrole-1,4-dione dibromide; 2,5-bis[2-[N-(methylimidazolium)-ethyl]]-3,6-bis(4-chlorophenyl)-pyrrolo-[3,4-c]pyrrole-1,4-dione dibromide; 2,5-bis[4-[N-(methylimidazolium)butyl]]-3,6-bis(4-chlorophenyl)-pyrrolo[3,4-c]pyrrole-1,4-dione dichloride; 2,5-bis[3-[N-(methylimidazolium)-propyl]]-3,6-bis(4-chlorophenyl)-pyrrolo[3,4-c]pyrrole-1,4-dione dichloride; 2,5-bis[2-[N-(methylimidazolium)ethyl]]-3,6-bis(4-chlorophenyl)-pyrrolo-[3,4-c]pyrrole-1,4-dione dichloride; 2,5-bis[4-[N-(methylimidazolium)butyl]]-3,6-bis(4-methyl-phenyl)-pyrrolo[3,4-c]pyrrole-1,4-dione dibromide; 2,5-bis[3-[N-(methylimidazolium)-propyl]]-3,6-bis(4-methyl-phenyl-pyrrolo-[3,4-c]pyrrole-1,4-dione dibromide; 2,5-bis[2-[N-(methylimidazolium)ethyl]]-3,6-bis(4-methyl-phenyl)-pyrrolo-[3,4-c]pyrrole-1,4-dione dibromide; 2,5-bis[4-[N-(methylimidazolium)butyl]]-3,6-bis(4-methyl-phenyl)-pyrrolo[3,4-c]pyrrole-1,4-dione dichloride; 2,5-bis[3-[N-(methylimidazolium)-propyl]]-3,6-bis(4-methyl-phenyl)-pyrrolo[3,4-c]pyrrole-1,4-dione dichloride; 2,5-bis[2-[N-(methylimidazolium)ethyl]]-3,6-bis(4-methyl-phenyl)-pyrrolo-[3,4-c]pyrrole-1,4-dione dichloride; 2,5-bis[4-[N-(methylimidazolium)-butyl]]-3,6-bis(3-cyano-phenyl)-pyrrolo[3,4-c]pyrrole-1,4-dione dibromide; 2,5-bis[3-[N-(methylimidazolium)-propyl]]-3,6-bis(3-cyano-phenyl)-pyrrolo-[3,4-c]pyrrole-1,4-dione dibromide; 2,5-bis[2-[N-(methylimidazolium)ethyl]]-3,6-bis(3-cyano-phenyl)-pyrrolo-[3,4-c]pyrrole-1,4-dione dibromide; 2,5-bis[4-[N-(methylimidazolium)butyl]]-3,6-bis(3-cyano-phenyl)-pyrrolo[3,4-c]pyrrole-1,4-dione dichloride; 2,5-bis[3-[N-(methylimidazolium)-propyl]]-3,6-bis(3-cyano-phenyl)-pyrrolo[3,4-c]pyrrole-1,4-dione dichloride; 2,5-bis[2-[N-(methylimidazolium)ethyl]]-3,6-bis(3-cyano-phenyl)-pyrrolo-[3,4-c]pyrrole-1,4-dione dichloride; 2,5-bis[4-[N-(methylimidazolium)butyl]]-3,6-bis(4-cyano-phenyl)-pyrrolo[3,4-c]pyrrole-1,4-dione dibromide; 2,5-bis[3-[N-(methylimidazolium)propyl]]-3,6-bis(4-cyano-phenyl)-pyrrolo-[3,4-c]pyrrole-1,4-dione dibromide; 2,5-bis[2-[N-(methylimidazolium)-ethyl]]-3,6-bis(4-cyano-phenyl)-pyrrolo-[3,4-c]pyrrole-1,4-dione dibromide; 2,5-bis[4-[N-(methylimidazolium)butyl]]-3,6-bis(4-cyano-phenyl)-pyrrolo[3,4-c]pyrrole-1,4-dione dichloride; 2,5-bis[3-[N-(methylimidazolium)-propyl]]-3,6-bis(4-cyano-phenyl)-pyrrolo[3,4-c]pyrrole-1,4-dione dichloride; 2,5-bis[2-[N-(methylimidazolium)-ethyl]]-3,6-bis(4-cyano-phenyl)-pyrrolo-[3,4-c]pyrrole-1,4-dione dichloride; 2,5-bis[4-[N-(methylimidazolium)butyl]]-3,6-bis(3,4-dichloro-phenyl)-pyrrolo[3,4-c]pyrrole-1,4-dione dibromide; 2,5-bis[3-[N-(methylimidazolium)-propyl]]-3,6-bis(3,4-dichloro-phenyl)-pyrrolo-[3,4-c]pyrrole-1,4-dione dibromide; 2,5-bis[2-[N-(methylimidazolium)ethyl]]-3,6-bis(3,4-dichloro-phenyl)-pyrrolo-[3,4-c]pyrrole-1,4-dione dibromide; 2,5-bis[4-[N-(methylimidazolium)butyl]]-3,6-bis(3,4-dichloro-phenyl)-pyrrolo[3,4-c]pyrrole-1,4-dione dichloride; 2,5-bis[3-[N-(methylimidazolium)-propyl]]-3,6-bis(3,4-dichloro-phenyl)-pyrrolo[3,4-c]pyrrole-1,4-dione dichloride; 2,5-bis[2-[N-(methylimidazolium)ethyl]]-3,6-bis(3,4-dichloro-phenyl)-pyrrolo-[3,4-c]pyrrole-1,4-dione dichloride; 2,5-bis[4-[N-(methylimidazolium)-butyl]]-3,6-bis(biphenyl)-pyrrolo[3,4-c]pyrrole-1,4-dione dibromide; 2,5-bis[3-[N-(methylimidazolium)propyl]]-3,6-bis(biphenyl)-pyrrolo[3,4-c]pyrrole-1,4-dione dibromide; 2,5-bis[2-[N-(methylimidazolium)ethyl]]-3,6-bis(biphenyl)-pyrrolo-[3,4-c]pyrrole-1,4-dione dibromide; 2,5-bis[4-[N-(methylimidazolium)-butyl]]-3,6-bis(biphenyl)-pyrrolo[3,4-c]pyrrole-1,4-dione dichloride; 2,5-bis[3-[N-(methylimidazolium)-propyl]]-3,6-bis(biphenyl)-pyrrolo[3,4-c]pyrrole-1,4-dione dichloride; 2,5-bis[2-[N-(methylimidazolium)ethyl]]-3,6-bis(biphenyl)-pyrrolo-[3,4-c]pyrrole-1,4-dione dichloride; 2,5-bis(4-trimethylammonium-butyl)-3,6-bis(4-methoxy-phenyl)-pyrrolo[3,4-c]pyrrole-1,4-dione dibromide; 2,5-bis(3-trimethylammonium-propyl)-3,6-bis(4-methoxy-phenyl)-pyrrolo[3,4-c]pyrrole-1,4-dione dibromide; 2,5-bis(2-trimethylammonium-ethyl)-3,6-bis(4-methoxy-phenyl)-pyrrolo[3,4-c]pyrrole-1,4-dione dibromide; 2,5-bis(4-trimethylammonium-butyl)-3,6-bis(4-methoxy-phenyl)-pyrrolo[3,4-c]pyrrole-1,4-dione dichloride; 2,5-bis(3-trimethylammonium-propyl)-3,6-bis(4-methoxy-phenyl)-pyrrolo[3,4-c]pyrrole-1,4-dione dichloride; 2,5-bis(2-trimethylammonium-ethyl)-3,6-bis(4-methoxy-phenyl)-pyrrolo-[3,4-c]pyrrole-1,4-dione dichloride; 2,5-bis[4-[4-(dimethylamino)pyridinium]butyl]-3,6-bis(4-methoxy-phenyl)-pyrrolo[3,4-c]pyrrole-1,4-dione dibromide; 2,5-bis[3-[4-(dimethyl-amino)-pyridinium]-propyl]-3,6-bis(4-methoxy-phenyl)-pyrrolo[3,4-c]pyrrole-1,4-dione dibromide; 2,5-bis[2-[4-(dimethylamino)pyridinium]ethyl]-3,6-bis(4-methoxy-phenyl)-pyrrolo[3,4-c]pyrrole-1,4-dione dibromide; 2,5-bis[4-[4-(dimethylamino)-pyridinium]butyl]-3,6-bis(4-methoxy-phenyl)-pyrrolo[3,4-c]pyrrole-1,4-dione dichloride; 2,5-bis[3-[4-(dimethylamino)pyridinium]propyl]-3,6-bis(4-methoxy-phenyl)-pyrrolo[3,4-c]pyrrole-1,4-dione dichloride; 2,5-bis[2-[4-(dimethylamino)-pyridinium]ethyl]-3,6-bis(4-methoxy-phenyl)-pyrrolo[3,4-c]pyrrole-1,4-dione dichloride; 2,5-bis(4-trimethylammonium-butyl)-3,6-bis(3-methoxy-phenyl)-pyrrolo[3,4-c]pyrrole-1,4-dione dibromide; 2,5-bis(3-trimethylammonium-propyl)-3,6-bis(3-methoxy-phenyl)-pyrrolo[3,4-c]pyrrole-1,4-dione dibromide; 2,5-bis(2-trimethylammonium-ethyl)-3,6-bis(3-methoxy-phenyl)-pyrrolo[3,4-c]pyrrole-1,4-dione dibromide; 2,5-bis(4-trimethylammonium-butyl)-3,6-bis(3-methoxy-phenyl)-pyrrolo[3,4-c]pyrrole-1,4-dione dichloride; 2,5-bis(3-trimethylammonium-propyl)-3,6-bis(3-methoxy-phenyl)-pyrrolo-[3,4-c]pyrrole-1,4-dione dichloride; 2,5-bis(2-trimethylammonium-ethyl)-3,6-bis(3-methoxy-phenyl)-pyrrolo-[3,4-c]pyrrole-1,4-dione dichloride; 2,5-bis[4-[4-

(dimethylamino)pyridinium]-butyl]-3,6-bis(3-methoxy-phenyl)-pyrrolo[3,4-c]pyrrole-1,4-dione dibromide; 2,5-bis[3-[4-(dimethylamino)-pyridinium]-propyl]-3,6-bis(3-methoxy-phenyl)-pyrrolo[3,4-c]pyrrole-1,4-dione dibromide; 2,5-bis[2-[4-(dimethylamino)pyridinium]ethyl]-3,6-bis(3-methoxy-phenyl)-pyrrolo[3,4-c]pyrrole-1,4-dione dibromide; 2,5-bis[4-[4-(dimethylamino)-pyridinium]butyl]-3,6-bis(3-methoxy-phenyl)-pyrrolo[3,4-c]pyrrole-1,4-dione dichloride; 2,5-bis[3-[4-(dimethylamino)pyridinium]propyl]-3,6-bis(3-methoxy-phenyl)-pyrrolo[3,4-c]pyrrole-1,4-dione dichloride; 2,5-bis[2-[4-(dimethylamino)-pyridinium]ethyl]-3,6-bis(3-methoxy-phenyl)-pyrrolo[3,4-c]pyrrole-1,4-dione dichloride; 2,5-bis(4-trimethylammonium-butyl)-3,6-bis(3,4-dichloro-phenyl)-pyrrolo[3,4-c]pyrrole-1,4-dione dibromide; 2,5-bis(3-trimethylammonium-propyl)-3,6-bis(3,4-dichloro-phenyl)-pyrrolo[3,4-c]pyrrole-1,4-dione dibromide; 2,5-bis(2-trimethylammonium-ethyl)-3,6-bis(3,4-dichloro-phenyl)-pyrrolo[3,4-c]pyrrole-1,4-dione dibromide; 2,5-bis(4-trimethylammonium-butyl)-3,6-bis(3,4-dichloro-phenyl)-pyrrolo[3,4-c]pyrrole-1,4-dione dichloride; 2,5-bis(3-trimethylammonium-propyl)-3,6-bis(3,4-dichloro-phenyl)-pyrrolo[3,4-c]pyrrole-1,4-dione dichloride; 2,5-bis(2-trimethylammonium-ethyl)-3,6-bis(3,4-dichloro-phenyl)-pyrrolo-[3,4-c]pyrrole-1,4-dione dichloride; 2,5-bis[4-[4-(dimethylamino)pyridinium]butyl]-3,6-bis(3,4-dichloro-phenyl)-pyrrolo[3,4-c]pyrrole-1,4-dione dibromide; 2,5-bis[3-[4-(dimethyl-amino)-pyridinium]-propyl]-3,6-bis(3,4-dichloro-phenyl)-pyrrolo[3,4-c]pyrrole-1,4-dione dibromide; 2,5-bis[2-[4-(dimethylamino)-pyridinium]ethyl]-3,6-bis(3,4-dichloro-phenyl)-pyrrolo[3,4-c]pyrrole-1,4-dione dibromide; 2,5-bis[4-[4-(dimethylamino)-pyridinium]butyl]-3,6-bis(3,4-dichloro-phenyl)-pyrrolo[3,4-c]pyrrole-1,4-dione dichloride; 2,5-bis[3-[4-(dimethylamino)pyridinium]propyl]-3,6-bis(3,4-dichloro-phenyl)-pyrrolo[3,4-c]pyrrole-1,4-dione dichloride; 2,5-bis[2-[4-(dimethylamino)-pyridinium]ethyl]-3,6-bis(3,4-dichloro-phenyl)pyrrolo-[3,4-c]pyrrole-1,4-dione dichloride.

Of the aforementioned compounds of formula (I), the following are preferred: 2,5-bis(4-trimethylammonium-butyl)-3,6-diphenyl-pyrrolo[3,4-c]pyrrole-1,4-dione dibromide; 2,5-bis(3-trimethylammonium-propyl)-3,6-diphenyl-pyrrolo[3,4-c]-pyrrole-1,4-dione dibromide; 2,5-bis(2-trimethylammonium-ethyl)-3,6-diphenyl-pyrrolo[3,4-c]pyrrole-1,4-dione dibromide; 2,5-bis(4-trimethylammonium-butyl)-3,6-diphenyl-pyrrolo[3,4-c]pyrrole-1,4-dione dichloride; 2,5-bis(3-trimethylammonium-propyl)-3,6-diphenyl-pyrrolo[3,4-c]pyrrole-1,4-dione dichloride; 2,5-bis(2-trimethyl-ammonium-ethyl)-3,6-diphenyl-pyrrolo[3,4-c]pyrrole-1,4-dione dichloride; 2,5-bis[4-[4-(dimethylamino)pyridinium]butyl]-3,6-diphenyl-pyrrolo[3,4-c]pyrrole-1,4-dione dibromide; 2,5-bis[3-[4-(dimethylamino)-pyridinium]propyl]-3,6-diphenyl-pyrrolo-[3,4-c]pyrrole-1,4-dione dibromide; 2,5-bis[2-[4-(dimethylamino)pyridinium]-ethyl]-3,6-diphenyl-pyrrolo[3,4-c]pyrrole-1,4-dione dibromide; 2,5-bis[4-[4-(dimethyl-amino)pyridinium]butyl]-3,6-diphenyl-pyrrolo[3,4-c]pyrrole-1,4-dione dichloride; 2,5-bis[3-[4-(dimethylamino)pyridinium]propyl]-3,6-diphenyl-pyrrolo[3,4-c]pyrrole-1,4-dione dichloride; 2,5-bis[2-[4-(dimethylamino)pyridinium]-ethyl]-3,6-diphenyl-pyrrolo[3,4-c]pyrrole-1,4-dione dichloride; 2,5-bis(4-trimethylammonium-butyl)-3,6-bis(4-chlorophenyl)-pyrrolo[3,4-c]pyrrole-1,4-dione dibromide; 2,5-bis(3-trimethyl-ammonium-propyl)-3,6-bis(4-chlorophenyl)-pyrrolo[3,4-c]pyrrole-1,4-dione dibromide; 2,5-bis(2-trimethylammonium-ethyl)-3,6-bis(4-chlorophenyl)-pyrrolo[3,4-c]pyrrole-1,4-dione dibromide; 2,5-bis(4-trimethylammonium-butyl)-3,6-bis(4-chlorophenyl)-pyrrolo[3,4-c]pyrrole-1,4-dione dichloride; 2,5-bis(3-trimethyl-ammonium-propyl)-3,6-bis(4-chlorophenyl)-pyrrolo[3,4-c]pyrrole-1,4-dione dichloride; 2,5-bis(2-trimethylammonium-ethyl)-3,6-bis(4-chlorophenyl)-pyrrolo-[3,4-c]pyrrole-1,4-dione dichloride; 2,5-bis[4-[4-(dimethylamino)pyridinium]butyl]-3,6-bis(4-chlorophenyl)-pyrrolo[3,4-c]pyrrole-1,4-dione dibromide; 2,5-bis[3-[4-(dimethylamino)pyridinium]propyl]-3,6-bis(4-chlorophenyl)-pyrrolo[3,4-c]pyrrole-1,4-dione dibromide; 2,5-bis[2-[4-(dimethylamino)pyridinium]ethyl]-3,6-bis(4-chlorophenyl)-pyrrolo[3,4-c]pyrrole-1,4-dione dibromide; 2,5-bis[4-[4-(dimethyl-amino)pyridinium]butyl]-3,6-bis(4-chlorophenyl)-pyrrolo[3,4-c]pyrrole-1,4-dione dichloride; 2,5-bis[3-[4-(dimethylamino)pyridinium]propyl]-3,6-bis(4-chlorophenyl)-pyrrolo[3,4-c]pyrrole-1,4-dione dichloride; 2,5-bis[2-[4-(dimethylamino)pyridinium]-ethyl]-3,6-bis(4-chlorophenyl)-pyrrolo[3,4-c]pyrrole-1,4-dione dichloride; 2,5-bis(4-trimethylammonium-butyl)-3,6-bis(4-methyl-phenyl)-pyrrolo[3,4-c]pyrrole-1,4-dione dibromide; 2,5-bis(3-trimethylammonium-propyl)-3,6-bis(4-methyl-phenyl)-pyrrolo-[3,4-c]pyrrole-1,4-dione dibromide; 2,5-bis(2-trimethylammonium-ethyl)-3,6-bis(4-methyl-phenyl)-pyrrolo[3,4-c]pyrrole-1,4-dione dibromide; 2,5-bis(4-trimethyl-ammonium-butyl)-3,6-bis(4-methyl-phenyl)-pyrrolo[3,4-c]pyrrole-1,4-dione dichloride; 2,5-bis(3-trimethylammonium-propyl)-3,6-bis(4-methyl-phenyl)-pyrrolo[3,4-c]pyrrole-1,4-dione dichloride; 2,5-bis(2-trimethylammonium-ethyl)-3,6-bis(4-methyl-phenyl)-pyrrolo[3,4-c]pyrrole-1,4-dione dichloride; 2,5-bis[4-[4-(dimethylamino)pyridinium]butyl]-3,6-bis(4-methyl-phenyl)-pyrrolo[3,4-c]pyrrole-1,4-dione dibromide; 2,5-bis[3-[4-(dimethylamino)pyridinium]propyl]-3,6-bis(4-methyl-phenyl)-pyrrolo[3,4-c]pyrrole-1,4-dione dibromide; 2,5-bis[2-[4-(dimethyl-amino)pyridinium]ethyl]-3,6-bis(4-methyl-phenyl)-pyrrolo[3,4-c]pyrrole-1,4-dione dibromide; 2,5-bis[4-[4-(dimethylamino)pyridinium]butyl]-3,6-bis(4-methyl-phenyl)-pyrrolo[3,4-c]pyrrole-1,4-dione dichloride; 2,5-bis[3-[4-(dimethylamino)pyridinium]-propyl]-3,6-bis(4-methyl-phenyl)-pyrrolo[3,4-c]pyrrole-1,4-dione dichloride; 2,5-bis[2-[4-(dimethylamino)pyridinium]ethyl]-3,6-bis(4-methyl-phenyl)-pyrrolo[3,4-c]pyrrole-1,4-dione dichloride; 2,5-bis(4-trimethylammonium-butyl)-3,6-bis(4-t-butyl-phenyl)-pyrrolo[3,4-c]pyrrole-1,4-dione dibromide; 2,5-bis(3-trimethyl-ammonium-propyl)-3,6-bis(4-t-butyl-phenyl)-pyrrolo[3,4-c]pyrrole-1,4-dione dibromide; 2,5-bis(2-trimethylammonium-ethyl)-3,6-bis(4-t-butyl-phenyl)-pyrrolo-[3,4-c]pyrrole-1,4-dione dibromide; 2,5-bis(4-trimethylammonium-butyl)-3,6-bis(4-t-butyl-phenyl)-pyrrolo[3,4-c]pyrrole-1,4-dione dichloride; 2,5-bis(3-trimethyl-ammonium-propyl)-3,6-bis(4-t-butyl-phenyl)-pyrrolo[3,4-c]pyrrole-1,4-dione dichloride; 2,5-bis(2-trimethylammonium-ethyl)-3,6-bis(4-t-butyl-phenyl)-pyrrolo-[3,4-c]pyrrole-1,4-dione dichloride; 2,5-bis[4-[4-(dimethylamino)pyridinium]-butyl]-3,6-bis(4-t-butyl-phenyl)-pyrrolo[3,4-c]pyrrole-1,4-dione dibromide; 2,5-bis[3-[4-(dimethylamino)pyridinium]propyl]-3,6-bis(4-t-butyl-phenyl)pyrrolo[3,4-c]pyrrole-1,4-dione dibromide; 2,5-bis[2-[4-(dimethylamino)pyridinium]ethyl]-3,6-bis(4-t-butyl-phenyl)-pyrrolo[3,4-c]pyrrole-1,4-dione dibromide; 2,5-bis[4-[4-(dimethyl-amino)pyridinium]butyl]-3,6-bis(4-t-butyl-phenyl)-pyrrolo[3,4-c]pyrrole-1,4-dione dichloride; 2,5-bis[3-[4-(dimethylamino)-pyridinium]-propyl]-3,6-bis(4-t-butyl-phenyl)-pyrrolo[3,4-c]pyrrole-1,4-dione dichloride; 2,5-bis[2-[4-(dimethylamino)-pyridinium]ethyl]-3,6- bis(4-t-butyl-phenyl)-pyrrolo[3,4-c]pyrrole-1,4-dione dichloride; 2,5-bis(4-trimethylammonium-butyl)-3,6-bis(biphenyl)-pyrrolo[3,4-c]pyrrole-1,4-dione dibromide; 2,5-bis(3-trimethylammonium-propyl)-3,6-bis(biphenyl)-pyrrolo[3,4-c]pyrrole-1,4-dione dibromide; 2,5-bis(2-trimethylammonium-ethyl)-3,6-bis(biphenyl)-pyrrolo[3,4-c]pyrrole-1,4-dione dibromide; 2,5-bis(4-trimethylammonium-butyl)-3,6-bis(biphenyl)-pyrrolo[3,4-c]pyrrole-1,4-dione dichloride; 2,5-bis(3-trimethylammonium-propyl)-3,6-bis(biphenyl)-pyrrolo[3,4-c]pyrrole-1,4-dione dichloride; 2,5-bis(2-trimethylammonium-ethyl)-3,6-bis-(biphenyl)-pyrrolo[3,4-c]pyrrole-1,4-dione dichloride; 2,5-bis[4-[4-(dimethylamino)-pyridinium]butyl]-3,6-bis(biphenyl)-pyrrolo[3,4-c]pyrrole-1,4-dione dibromide; 2,5-bis[3-[4-(dimethylamino)pyridinium]propyl]-3,6-bis(biphenyl)-pyrrolo[3,4-c]pyrrole-1,4-dione dibromide; 2,5-bis[2-[4-(dimethylamino)-pyridinium]ethyl]-3,6-bis-(biphenyl)-pyrrolo[3,4-c]pyrrole-1,4-dione dibromide; 2,5-bis[4-[4-(dimethylamino)-pyridinium]butyl]-3,6-bis(biphenyl)-pyrrolo[3,4-c]pyrrole-1,4-dione dichloride; 2,5-bis[3-[4-(dimethylamino)-pyridinium]propyl]-3,6-bis(biphenyl)-pyrrolo[3,4-c]-pyrrole-1,4-dione dichloride; 2,5-bis[2-[4-(dimethylamino)pyridinium]ethyl]-3,6-bis(biphenyl)-pyrrolo[3,4-c]pyrrole-1,4-dione dichloride; 2,5-bis(4-trimethyl-ammonium-butyl)-3,6-bis(4-dimethylamino-phenyl)pyrrolo[3,4-c]pyrrole-1,4-dione dibromide; 2,5-bis(3-trimethylammonium-propyl)-3,6-bis(4-dimethylamino-phenyl)-pyrrolo[3,4-c]pyrrole-1,4-dione dibromide; 2,5-bis(2-trimethylammonium-ethyl)-3,6-bis(4-dimethylamino-phenyl)-pyrrolo[3,4-c]pyrrole-1,4-dione dibromide; 2,5-bis(4-trimethylammonium-butyl)-3,6-bis(4-dimethylamino-phenyl)-pyrrolo[3,4-c]pyrrole-1,4-dione dichloride; 2,5-bis(3-trimethylammonium-propyl)-3,6-bis(4-dimethyl-amino-phenyl)-pyrrolo[3,4-c]pyrrole-1,4-dione dichloride; 2,5-bis(2-trimethyl-ammonium-ethyl)-3,6-bis(4-dimethylamino-phenyl)pyrrolo[3,4-c]pyrrole-1,4-dione dichloride; 2,5-bis[4-[4-(dimethylamino)pyridinium]butyl]-3,6-bis(4-dimethylamino-phenyl)-pyrrolo[3,4-c]pyrrole-1,4-dione dibromide; 2,5-bis[3-[4-(dimethylamino)-pyridinium]propyl]-3,6-bis(4-dimethylaminophenyl)-pyrrolo[3,4-c]pyrrole-1,4-dione dibromide; 2,5-bis[2-[4-(dimethylamino)pyridinium]ethyl]-3,6-bis(4-dimethylamino-phenyl)-pyrrolo[3,4-c]pyrrole-1,4-dione dibromide; 2,5-bis[4-[4-(dimethylamino)-pyridinium]butyl]-3,6-bis(4-dimethylamino-phenyl)-pyrrolo[3,4-c]pyrrole-1,4-dione dichloride; 2,5-bis[3-[4-(dimethylamino)-pyridinium]propyl]-3,6-bis(4-dimethyl-amino-phenyl)-pyrrolo[3,4-c]pyrrole-1,4-dione dichloride; 2,5-bis[2-[4-(dimethyl-amino)pyridinium]ethyl]-3,6-bis(4-dimethylaminophenyl)pyrrolo[3,4-c]pyrrole-1,4-dione dichloride; 2,5-bis[4-[N-(methylimidazolium)butyl]]-3,6-diphenyl-pyrrolo[3,4-c]pyrrole-1,4-dione dibromide; 2,5-bis[3-[N-(methylimidazolium)propyl]]-3,6-diphenyl-pyrrolo[3,4-c]pyrrole-1,4-dione dibromide; 2,5-bis[2-[N-(methylimidazolium)ethyl]]-3,6-diphenyl-pyrrolo[3,4-c]pyrrole-1,4-dione dibromide; 2,5-bis[4-[N-(methylimidazolium)butyl]]-3,6-diphenyl-pyrrolo[3,4-c]pyrrole-1,4-dione dichloride; 2,5-bis[3-[N-(methylimidazolium)-propyl]]-3,6-diphenyl-pyrrolo[3,4-c]pyrrole-1,4-dione dichloride; 2,5-bis[2-[N-(methylimidazolium)ethyl]]-3,6-diphenyl-pyrrolo[3,4-c]pyrrole-1,4-dione dichloride; 2,5-bis[4-[N-(methylimidazolium)-butyl]]-3,6-bis(4-t-butyl-phenyl)-pyrrolo[3,4-c]pyrrole-1,4-dione dibromide; 2,5-bis[3-[N-(methylimidazolium)propyl]]-3,6-bis(4-t-butyl-phenyl)-pyrrolo[3,4-c]pyrrole-1,4-dione dibromide; 2,5-bis[2-[N-(methylimidazolium)ethyl]]-3,6-bis(4-t-butyl-phenyl)-pyrrolo[3,4-c]pyrrole-1,4-dione dibromide; 2,5-bis[4-[N-(methylimidazolium)butyl]]-3,6-bis(4-t-butyl-phenyl)-pyrrolo[3,4-c]pyrrole-1,4-dione dichloride; 2,5-bis[3-[N-(methylimidazolium)-propyl]]-3,6-bis(4-t-butyl-phenyl)-pyrrolo[3,4-c]pyrrole-1,4-dione dichloride; 2,5-bis[2-[N-(methylimidazolium)ethyl]]-3,6-bis(4-t-butyl-phenyl)-pyrrolo[3,4-c]pyrrole-1,4-dione dichloride; 2,5-bis[4-[N-(methylimidazolium)-butyl]]-3,6-bis(4-chlorophenyl)-pyrrolo[3,4-c]pyrrole-1,4-dione dibromide; 2,5-bis[3-[N-(methylimidazolium)propyl]]-3,6-bis(4-chlorophenyl)-pyrrolo[3,4-c]pyrrole-1,4-dione dibromide; 2,5-bis[2-[N-(methylimidazolium)-ethyl]]-3,6-bis(4-chlorophenyl)-pyrrolo[3,4-c]pyrrole-1,4-dione dibromide; 2,5-bis[4-[N-(methylimidazolium)butyl]]-3,6-bis(4-chlorophenyl)-pyrrolo[3,4-c]pyrrole-1,4-dione dichloride; 2,5-bis[3-[N-(methylimidazolium)-propyl]]-3,6-bis(4-chloro-phenyl)-pyrrolo[3,4-c]pyrrole-1,4-dione dichloride; 2,5-bis[2-[N-(methylimidazolium)ethyl]]-3,6-bis(4-chlorophenyl)-pyrrolo[3,4-c]pyrrole-1,4-dione dichloride; 2,5-bis[4-[N-(methylimidazolium)butyl]]-3,6-bis(4-methyl-phenyl)-pyrrolo[3,4-c]pyrrole-1,4-dione dibromide; 2,5-bis[3-[N-(methylimidazolium)-propyl]]-3,6-bis(4-methyl-phenyl)-pyrrolo[3,4-c]pyrrole-1,4-dione dibromide; 2,5-bis[2-[N-(methylimidazolium)ethyl]]-3,6-bis(4-methyl-phenyl)pyrrolo[3,4-c]pyrrole-1,4-dione dibromide; 2,5-bis[4-[N-(methylimidazolium)butyl]]-3,6-bis(4-methyl-phenyl)-pyrrolo[3,4-c]pyrrole-1,4-dione dichloride; 2,5-bis[3-[N-(methylimidazolium)-propyl]]-3,6-bis(4-methyl-phenyl)-pyrrolo[3,4-c]pyrrole-1,4-dione dichloride; 2,5-bis[2-[N-(methylimidazolium)ethyl]]-3,6-bis(4-methyl-phenyl)-pyrrolo[3,4-c]pyrrole-1,4-dione dichloride; 2,5-bis[4-[N-(methylimidazolium)-butyl]]-3,6-bis(3-cyano-phenyl)-pyrrolo[3,4-c]pyrrole-1,4-dione dibromide; 2,5-bis[3-[N-(methylimidazolium)propyl]]-3,6-bis(3-cyano-phenyl)pyrrolo[3,4-c]pyrrole-1,4-dione dibromide; 2,5-bis[2-[N-(methylimidazolium)ethyl]]-3,6-bis(3-cyano-phenyl)-pyrrolo[3,4-c]pyrrole-1,4-dione dibromide; 2,5-bis[4-[N-(methylimidazolium)-butyl]]-3,6-bis(3-cyano-phenyl)-pyrrolo[3,4-c]pyrrole-1,4-dione dichloride; 2,5-bis[3-[N-(methylimidazolium)-propyl]]-3,6-bis(3-cyano-phenyl)-pyrrolo[3,4-c]pyrrole-1,4-dione dichloride; 2,5-bis[2-[N-(methylimidazolium)-ethyl]]-3,6-bis(3-cyano-phenyl)-pyrrolo[3,4-c]pyrrole-1,4-dione dichloride; 2,5-bis[4-[N-(methylimidazolium)butyl]]-3,6-bis(4-cyano-phenyl)-pyrrolo[3,4-c]pyrrole-1,4-dione dibromide; 2,5-bis[3-[N-(methylimidazolium)-propyl]]-3,6-bis(4-cyano-phenyl)-pyrrolo[3,4-c]pyrrole-1,4-dione dibromide; 2,5-bis[2-[N-(methylimidazolium)ethyl]]-3,6-bis(4-cyano-phenyl)-pyrrolo[3,4-c]pyrrole-1,4-dione dibromide; 2,5-bis[4-[N-(methylimidazolium)butyl]]-3,6-bis(4-cyano-phenyl)pyrrolo[3,4-c]pyrrole-1,4-dione dichloride; 2,5-bis[3-[N-(methylimidazolium)-propyl]]-3,6-bis(4-cyano-phenyl)-pyrrolo[3,4-c]pyrrole-1,4-dione dichloride; 2,5-bis[2-[N-(methylimidazolium)ethyl]]-3,6-bis(4-cyano-phenyl)-pyrrolo[3,4-c]pyrrole-1,4-dione dichloride; 2,5-bis-[4-[N-(methylimidazolium)-butyl]]-3,6-bis(3,4-dichloro-phenyl)-pyrrolo[3,4-c]pyrrole-1,4-dione dibromide; 2,5-bis[3-[N-(methylimidazolium)propyl]]-3,6-bis(3,4-dichloro-phenyl)pyrrolo[3,4-c]pyrrole-1,4-dione dibromide; 2,5-bis[2-[N-(methylimidazolium)ethyl]]-3,6-bis(3,4-dichloro-phenyl)-pyrrolo[3,4-c]pyrrole-1,4-dione dibromide; 2,5-bis[4-[N-(methylimidazolium)butyl]]-3,6-bis(3,4-dichloro-phenyl)-pyrrolo[3,4-c]pyrrole-1,4-dione dichloride; 2,5-bis[3-[N-(methylimidazolium)-propyl]]-3,6-bis(3,4-dichloro-phenyl)-pyrrolo[3,4-c]pyrrole-1,4-dione dichloride; 2,5-bis-[2-[N-(methylimidazolium)-ethyl]]-3,6-bis(3,4-dichlorophenyl)-pyrrolo[3,4-c]pyrrole-1,4-dione dichloride; 2,5-bis[4-[N-(methylimidazolium)butyl]]-3,6-bis(biphenyl)-pyrrolo[3,4-c]pyrrole-1,4-dione dibromide; 2,5-bis[3-[N-(methylimidazolium)propyl]]-3,6-bis(biphenyl)-pyrrolo[3,4-c]pyrrole-1,4-dione dibromide; 2,5-bis[2-[N-(methylimidazolium)-ethyl]]-3,6-bis(biphenyl)-pyrrolo[3,4-c]pyrrole-1,4-dione dibromide; 2,5-bis[4-[N-(methylimidazolium)butyl]]-3,6-bis(biphenyl)-pyrrolo[3,4-c]pyrrole-1,4-dione dichloride; 2,5-bis[3-[N-(methylimidazolium)-propyl]]-3,6-bis(biphenyl)-pyrrolo[3,4-c]pyrrole-1,4-dione dichloride; 2,5-bis[2-[N-(methylimidazolium)-ethyl]]-3,6-bis(biphenyl)-pyrrolo[3,4-c]pyrrole-1,4-dione dichloride; 2,5-bis(4-trimethyl-ammonium-butyl)-3,6-bis(3,4-dichloro-phenyl)-pyrrolo[3,4-c]pyrrole-1,4-dione dibromide; 2,5-bis(3-trimethylammonium-propyl)-3,6-bis(3,4-dichloro-phenyl)-pyrrolo[3,4-c]pyrrole-1,4-dione dibromide; 2,5-bis(2-trimethylammonium-ethyl)-3,6-bis(3,4-dichloro-phenyl)-pyrrolo[3,4-c]pyrrole-1,4-dione dibromide; 2,5-bis(4-trimethylammonium-butyl)-3,6-bis(3,4-dichloro-phenyl)-pyrrolo[3,4-c]pyrrole-1,4-dione dichloride; 2,5-bis(3-trimethylammonium-propyl)-3,6-bis(3,4-dichloro-phenyl)-pyrrolo[3,4-c]pyrrole-1,4-dione dichloride; 2,5-bis(2-trimethylammonium-ethyl)-3,6-bis(3,4-dichloro-phenyl)-pyrrolo[3,4-c]pyrrole-1,4-dione dichloride; 2,5-bis[4-[4-(dimethylamino)pyridinium]-butyl]-3,6-bis(3,4-dichloro-phenyl)-pyrrolo[3,4-c]pyrrole-1,4-dione dibromide; 2,5-bis[3-[4-(dimethylamino)-pyridinium]-propyl]-3,6-bis(3,4-dichloro-phenyl)-pyrrolo[3,4-c]pyrrole-1,4-dione dibromide; 2,5-bis[2-[4-(dimethylamino)-pyridinium]ethyl]-3,6-bis(3,4-dichloro-phenyl)-pyrrolo[3,4-c]pyrrole-1,4-dione dibromide; 2,5-bis[4-[4-(dimethylamino)-pyridinium]butyl]-3,6-bis(3,4-dichloro-phenyl)-pyrrolo[3,4-c]pyrrole-1,4-dione dichloride; 2,5-bis[3-[4-(dimethylamino)pyridinium]propyl]-3,6-bis(3,4-dichloro-phenyl)-pyrrolo[3,4-c]pyrrole-1,4-dione dichloride; 2,5-bis[2-[4-(dimethylamino)-pyridinium]ethyl]-3,6-bis(3,4-dichloro-phenyl)-pyrrolo[3,4-c]pyrrole-1,4-dione dichloride; 2,5-bis(4-trimethylammonium-butyl)-3,6-bis(4-cyano-phenyl)-pyrrolo[3,4-c]pyrrole-1,4-dione dibromide; 2,5-bis(3-trimethylammonium-propyl)-3,6-bis(4-cyano-phenyl)-pyrrolo-[3,4-c]pyrrole-1,4-dione dibromide; 2,5-bis(2-trimethylammonium-ethyl)-3,6-bis(4-cyano-phenyl)-pyrrolo[3,4-c]pyrrole-1,4-dione dibromide; 2,5-bis(4-trimethyl-ammonium-butyl)-3,6-bis(4-cyano-phenyl)-pyrrolo[3,4-c]pyrrole-1,4-dione dichloride; 2,5-bis(3-trimethylammonium-propyl)-3,6-bis(4-cyano-phenyl)-pyrrolo[3,4-c]pyrrole-1,4-dione dichloride; 2,5-bis(2-trimethylammonium-ethyl)-3,6-bis(4-cyano-phenyl)-pyrrolo[3,4-c]pyrrole-1,4-dione dichloride; 2,5-bis[4-[4-(dimethylamino)pyridinium]butyl]-3,6-bis(4-cyano-phenyl)-pyrrolo[3,4-c]pyrrole-1,4-dione dibromide; 2,5-bis[3-[4-(dimethylamino)-pyridinium]propyl]-3,6-bis(4-cyano-phenyl)-pyrrolo[3,4-c]pyrrole-1,4-dione dibromide; 2,5-bis[2-[4-(dimethyl-amino)pyridinium]ethyl]-3,6-bis(4-cyano-phenyl-pyrrolo[3,4-c]pyrrole-1,4-dione dibromide; 2,5-bis[4-[4-(dimethylamino)pyridinium]butyl]-3,6-bis(4-cyano-phenyl)-pyrrolo[3,4-c]pyrrole-1,4-dione dichloride; 2,5-bis[3-[4-(dimethylamino)-pyridinium]propyl]-3,6-bis(4-cyano-phenyl)-pyrrolo[3,4-c]pyrrole-1,4-dione dichloride; 2,5-bis[2-[4-(dimethylamino)pyridinium]ethyl]-3,6-bis(4-cyano-phenyl)-pyrrolo[3,4-c]pyrrole-1,4-dione dichloride; 2,5-bis(4-trimethylammonium-butyl)-3,6-bis(3-cyano-phenyl)-pyrrolo[3,4-c]pyrrole-1,4-dione dibromide; 2,5-bis(3-trimethyl-ammonium-propyl)-3,6-bis(3-cyano-phenyl)-pyrrolo[3,4-c]pyrrole-1,4-dione dibromide; 2,5-bis(2-trimethylammonium-ethyl-3,6-bis(3-cyano-phenyl)-pyrrolo[3,4-c]pyrrole-1,4-dione dibromide; 2,5-bis(4-trimethylammonium-butyl)-3,6-bis(3-cyano-phenyl)-pyrrolo[3,4-c]pyrrole-1,4-dione dichloride; 2,5-bis(3-trimethylammonium-propyl)-3,6-bis(3-cyano-phenyl)-pyrrolo[3,4-c]pyrrole-1,4-dione dichloride; 2,5-bis(2-trimethylammonium-ethyl)-3,6-bis(3-cyano-phenyl)-pyrrolo[3,4-c]pyrrole-1,4-dione dichloride; 2,5-bis[4-[4-(dimethylamino)pyridinium]butyl]-3,6-bis(3-cyano-phenyl)-pyrrolo[3,4-c]pyrrole-1,4-dione dibromide; 2,5-bis[3-[4-(dimethylamino)-pyridinium]-propyl]-3,6-bis(3-cyano-phenyl)-pyrrolo[3,4-c]pyrrole-1,4-dione dibromide; 2,5-bis[2-[4-(dimethylamino)pyridinium]ethyl]-3,6-bis(3-cyano-phenyl)-pyrrolo[3,4-c]pyrrole-1,4-dione dibromide; 2,5-bis[4-[4-(dimethylamino)-pyridinium]butyl]-3,6-bis(3-cyano-phenyl)-pyrrolo[3,4-c]pyrrole-1,4-dione dichloride; 2,5-bis[3-[4-(dimethylamino)pyridinium]propyl]-3,6-bis(3-cyano-phenyl)-pyrrolo[3,4-c]pyrrole-1,4-dione dichloride; 2,5-bis[2-[4-(dimethylamino)pyridinium]-ethyl]-3,6-bis(3-cyano-phenyl)-pyrrolo[3,4-c]pyrrole-1,4-dione dichloride.

Especially preferred compounds of Formula (I) are 2,5-bis(4-trimethylammonium-butyl)-3,6-diphenyl-pyrrolo[3,4-c]pyrrole-1,4-dione dibromide, 2,5-bis(4-trimethylammonium-butyl)-3,6-diphenyl-pyrrolo[3,4-c]pyrrole-1,4-dione dichloride, 2,5-bis(4-trimethylammonium-butyl)-3,6-bis[4-(dimethylamino)phenyl]-pyrrolo[3,4-c]pyrrole-1,4-dione dibromide, 2,5-bis(4-trimethylammonium-butyl)-3,6-bis[4-(dimethylamino)phenyl]-pyrrolo[3,4-c]pyrrole-1,4-dione dichloride, 2,5-bis[4-[4-(dimethylamino)pyridinium]butyl]-3,6-diphenyl-pyrrolo[3,4-c]pyrrole-1,4-dione dibromide; 2,5-bis[4-[4-(dimethylamino)pyridinium]butyl]-3,6-diphenyl-pyrrolo[3,4-c]pyrrole-1,4-dione dichloride; 2,5-bis[4-[N-(methylimidazolium)butyl]]-3,6-diphenyl-pyrrolo[3,4-c]pyrrole-1,4-dione dibromide and 2,5-bis[4-[N-(methylimidazolium)butyl]]-3,6-diphenyl-pyrrolo[3,4-c]pyrrole-1,4-dione dichloride.

The inventive dye derivatives of formula (I) can be synthesized easily by introducing a cationic group in the diketopyrrolopyrroles of formula (II), in which the $Q_1$ and $Q_2$ groups have the same meaning as in formula (I).

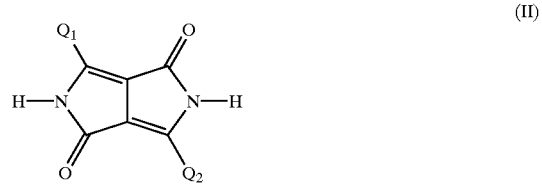

(II)

The object of the present invention therefore also is a method for producing cationic pyrrolopyrrole derivative of formula (I), as shown in outline 1, for which initially the NH group in the compound of formula (II) is reacted with an alkyl dihalide and, subsequently, the halogen derivatives obtained is reacted with a suitable tertiary amine or a suitable tertiary phosphororganic compound ("tertiary phosphine").

Outline 1

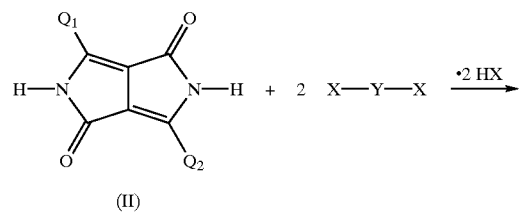

(II)

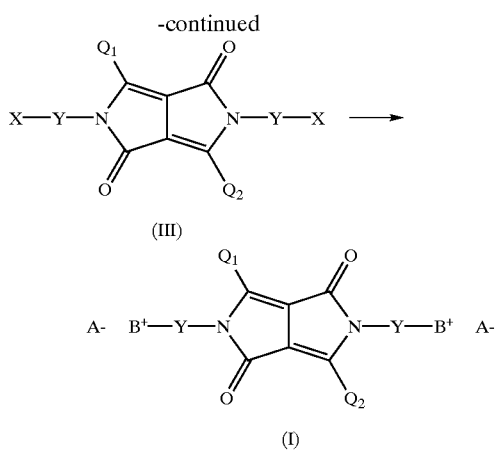

(III)

(I)

The synthesis of compounds of formula (I) starts out from compounds of formula (II), which are commercially available or can be synthesized easily, by reacting the compound of formula (II) with the appropriate alkyl dihalide in the presence of a base, such as sodium hydride, in an aprotic, polar solvent, such as dimethylformamide, dimethylacetamide, N-methylpyrrolidone or dimethyl sulfoxide, the NH group being halogenated. Subsequently, the compound of formula (III) obtained is reacted with a tertiary amine or a tertiary phosphine to form the cationic pyrrolo-pyrrole derivative of formula (I). The reaction of the compound of formula (III) with the tertiary amine or the tertiary phosphine preferably takes place in a solvent such as ethanol, toluene, dioxane, dimethylformamide, dimethylacetamide, N-methylpyrrolidone, acetonitrile or dimethyl sulfoxide. The synthesis method of outline 1 can be carried out in one step (that is, without isolating the compounds of formula (III)), as well as in two steps (that is, with isolating the compound of formula (III)).

Likewise, it is possible to synthesize the cationic pyrrolo-pyrrole derivative of formula (I) by a one-step method of outline 2, for which the NH group of compounds of formula (II) is reacted to with a previously formed cationic chain, such as bromobutane-4-trimethylammonium bromide. The method of outline 1, however, is preferred.

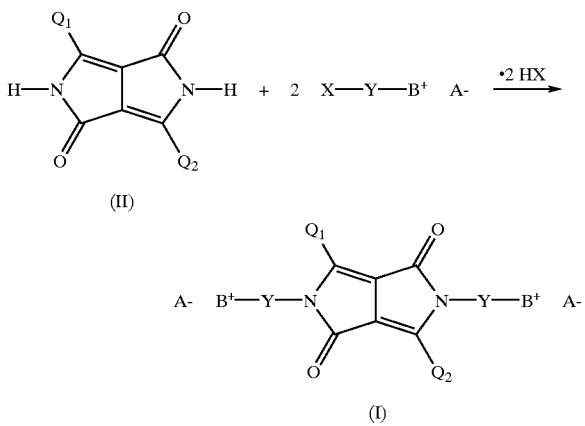

(II)

(I)

The groups z, $Q_1$, $Q_2$, Y, $A^-$ and $B^-$, used in outlines 1 and 2, have the same meaning as in formula (1), while A represents an uncharged group, which corresponds to the anion $A^-$, and B represents an appropriate tertiary amine or phosphine and X represents a halogen atom, preferably a chlorine or bromine atom.

If the alkyl dihalide (method of outline 1) or the previously formed cationic chain (method of outline 2) is used in a molar deficiency, the compound of formula (I), in which R1 or R2 are hydrogen, can also be synthesized by this method.

The following compounds, for example, can be used as compound of formula (II):

2,5-dihydro-3,6-diphenyl-pyrrolo[3,4-c]pyrrole-1,4-dione;
3,6-bis[1,1'-(biphenyl)-4-yl]-2,5-dihydro-pyrrolo[3,4-c]pyrrole-1,4-dione;
3,6-bis(4-chlorophenyl)-2,5-dihydro-pyrrolo[3,4-c]pyrrole-1,4-dione;
3,6-bis(3-chlorophenyl)-2,5-dihydro-pyrrolo[3,4-c]pyrrole-1,4-dione;
3,6-bis(4-methylphenyl)-2,5-dihydro-pyrrolo[3,4-c]pyrrole-1,4-dione;
3,6-bis(3-methylphenyl)-2,5-dihydro-pyrrolo[3,4-c]pyrrole-1,4-dione;
3,6-bis(4-t-butylphenyl)-2,5-dihydro-pyrrolo[3,4-c]pyrrole-1,4-dione;
3,6-bis[4-(dimethylamino)phenyl]-2,5-dihydro-pyrrolo[3,4-c]pyrrole-1,4-dione;
3,6-bis(4-cyanophenyl)-2,5-dihydro-pyrrolo[3,4-c]pyrrole-1,4-dione;
3,6-bis(3-cyanophenyl)-2,5-dihydro-pyrrolo[3,4-c]pyrrole-1,4-dione;
3,6-bis(3,4-dichlorophenyl)-2,5-dihydro-pyrrolo[3,4-c]pyrrole-1,4-dione;
3,6-bis(4-methoxyphenyl)-2,5-dihydro-pyrrolo[3,4-c]pyrrole-1,4-dione and 3,6-bis(3-methoxyphenyl)-2,5-dihydro-pyrrolo[3,4-c]pyrrole-1,4-dione.

The new cationic pyrrolo-pyrrole derivatives of formula (I) have excellent water solubility and make uniform dyeing of keratin fibers possible with good resistance to light, sweat and shampooing. The inventive derivatives of formula (I) enable keratin fibers, especially human hair, but also wool or fur, to be dyed an intensive, brilliant coloration under gentle, skin-compatible conditions. If stimulated appropriately, for example, by UV light or sunlight, the dyeing obtained can fluoresce.

A further object of the present invention therefore is an agent for dyeing keratin fibers, especially human hair, wherein at least one cationic pyrrolo-pyrrole derivative of the general formula (I) is contained.

The cationic pyrrolo-pyrrole derivatives of formula (I) are contained in the inventive dyeing agents preferably in an amount 0.01 to 10% by weight and especially of 0.1 to 8% by weight.

Aside from the dyes of formula (I), the inventive dyeing agent may additionally contain other known direct dyes from the group consisting of plant dyes, nitro dyes, azo dyes, anthraquinone dyes and triphenylmethane dyes, alone or in admixture with other, such as henna, indigo, chamomile flowers, curcuma roots, rhubarb, black alder bark, olive leaves, Canadian bloodroot, goldenseal, gopherwood, redwood, red sandalwood, logwood, madder root, black elderberry or black chokeberry, 1,4-bis[(2-hydroxyethyl)amino]-2-nitrobenzene; 1-amino-3-methyl-4-[(2-hydroxyethyl)amino]-6-nitrobenzene (HC Violet No. 1); 1-(2-hydroxyethyl)-amino-2-nitro-4-[di(2-hydroxyethyl)amino]-benzene (HC Blue No. 2); 4-[ethyl-(2-hydroxyethyl)amino]-1-[(2-hydroxyethyl)amino]-2-nitrobenzene hydrochloride (HC Blue No. 12); 4-[di(2-hydroxyethyl)amino]-1-[(2-methoxyethyl)amino]-2-nitrobenzene (HC Blue No. 11); 1-[(2,3-dihydroxypropyl)amino]-4-[methyl-(2- hydroxyethyl)amino]-2-nitrobenzene (HC Blue No. 10); 1-[(2,3-dihydroxypropyl)amino]-4-[ethyl-(2-hydroxyethyl) amino]-2-nitrobenzene hydrochloride (HC Blue No. 9); 1-(3-hydroxypropylamino)-4-[di(2-hydroxyethyl)amino]-2-nitrobenzene (HC Violet No. 2); 1-methylamino-4-[methyl-(2,3-dihydroxypropyl)amino]-2-nitrobenzene (HC Blue No. 6); 2-((4-amino-2-nitrophenyl)amino)-5-dimethyl-amino-benzoic acid (HC Blue No. 13); 1-(2-aminoethylamino)-4-[di(2-hydroxyethyl)amino]-2-nitrobenzene; 4-(di(2-hydroxy-ethyl)amino)-2-nitro-1-phenylamino-benzene; 4-amino-2-nitro-diphenylamine (HC Red No. 1); 1-amino-4-[(2-hydroxyethyl)amino]-2-nitrobenzene (HC Red No. 7); 2-amino-4,6-dinitro-phenol; 4-amino-1-[(2-hydroxyethyl) amino]-2-nitrobenzene (HC Red No. 3); 1-amino-5-chloro-4-[(2,3-dihydroxypropyl)-amino]-2-nitrobenzene (HC Red No. 10); 5-chloro-1,4-[di(2,3-dihydroxy-propyl)amino]-2-nitrobenzene (HC Red No. 11); 1-amino-4-[di(2-hydroxyethyl)amino]-2-nitrobenzene hydrochloride (HC Red No. 13); 7-amino-3,4-dihydro-6-nitro-2H-1,4-benzoxazine (HC Red No. 14); 1-amino-5-chloro-4-[(2-hydroxyethyl)-amino]-2-nitrobenzene; 1-amino-4-((2,3-dihydroxypropyl)amino)-5-methyl-2-nitrobenzene; 4-amino-2-nitro-1-((prop-2-en-1-yl)amino)-benzene; 4-amino-3-nitrophenol; 4-[(2-hydroxyethyl)-amino]-3-nitro-phenol; 1-[(2-aminoethyl)-amino]-4-(2-hydroxyethoxy)-2-nitrobenzene (HC Orange No. 2); 4-(2,3-dihydroxypropoxy)-1-[(2-hydroxyethyl)amino]-2-nitrobenzene (HC Orange No. 3); 2-[(2-hydroxyethyl) amino]-4,6-dinitro-phenol; 4-ethylamino-3-nitrobenzoic acid; 2-[(amino-2-nitrophenyl)amino]-benzoic acid; 2-chloro-6-ethylamino-4-nitrophenol; 2-amino-6-chloro-4-nitrophenol; 4-[(3-hydroxypropyl)-amino]-3-nitrophenol; 2,5-diamino-6-nitropyridine; 6-amino-3-((2-hydroxyethyl)-amino)-2-nitropyridine; 3-amino-6-((2-hydroxyethyl) amino)-2-nitropyridine; 3-amino-6-(ethylamino)-2-nitropyridine; 3-((2-hydroxyethyl)-amino)-6-(methylamino)-2-nitropyridine; 3-amino-6-(methylamino)-2-nitropyridine; 6-(ethylamino)-3-((2-hydroxyethyl) amino)-2-nitropyridine; 1,2,3,4-tetra-hydro-6-nitroquinoxaline; 4-[(2-hydroxyethyl)-amino]-3-nitro-1-methylbenzene; 1-[(2-hydroxyethyl)-amino]-2-nitrobenzene (HC Yellow No. 2); 1-(2-hydroxyethoxy)-2-[(2-hydroxyethyl)amino]-5-nitrobenzene (HC Yellow No. 4); 1-amino-2-[(2-hydroxyethyl)amino]-5-nitrobenzene (HC Yellow No. 5); 4-[(2,3-dihydroxy-propyl)amino]-3-nitro-1-trifluoro-methylbenzene (HC Yellow No. 6); 2-[(2-hydroxyethyl)amino]-1-methoxy-5-nitrobenzene; 2-amino-3-nitro-phenol; 2,3-(dihydroxypropoxy)-3-methylamino-4-nitrobenzene; 1-amino-4-((2-aminoethyl)amino)-5-methyl-2-nitrobenzene; 3-[(2-aminoethyl)amino]-1-methoxy-4-nitrobenzene hydrochloride (HC Yellow No. 9); 1-[(2-ureidoethyl)-amino]-4-nitrobenzene; 1-chloro-2,4-bis[(2-hydroxyethyl)-amino]-5-nitrobenzene (HC Yellow No. 10); 2-[(2-hydroxyethyl)amino]-5-nitrophenol (HC Yellow No. 11); 1-chloro-4-[(2-hydroxyethyl)amino]-3-nitrobenzene (HC Yellow No. 12); 4-[(2-hydroxyethyl)amino]-3-nitro-1-trifluoromethylbenzene (HC Yellow No. 13); 4-[(2-hydroxyethyl)-amino]-3-nitro-benzonitrile (HC Yellow 14); 4[(2-hydroxyethyl)amino]-3-nitro-benzamide (HC Yellow No. 15); 1,4-di[(2,3-dihydroxypropyl)amino]-9,10-anthraquinone; 1-[(2-hydroxyethyl)amino]-4-methyl-amino-9,10-anthraquinone (CI61505, Disperse Blue No. 3); 2-[(2-aminoethyl)-amino]-9,10-anthraquinone (HC Orange No. 5); 1-hydroxy-4-[(4-methyl-2-sulfophenyl) amino]-9,10-anthraquinone; 1[(3-aminopropyl)amino]-4-methylamino-9,10-anthraquinone (HC Blue No. 8); 1-[(3-aminopropyl)-amino]-9,10-anthraquinone (HC Red No. 8); 1,4-diamino-2-methoxy-9,10-anthraquinone (CI62015, Disperse Red No. 11); 1,4-dihydroxy-5,8-bis[(2-hydroxyethyl) amino]-9,10-anthraquinone (CI62500, Disperse Blue No. 7); 1,4-diamino-9,10-anthraquinone (CI61100, Disperse Violet No. 1); 1-amino-4-(methylamino)-9,10-anthraquinone (CI61105, Disperse Violet No. 4); 9-(dimethylamino)-benzo[a]phenoxazine-7-ium chloride (CI 51175; Basic Blue No. 6); di[4-(diethylamino)phenyl] [4-(ethylamino)naphthyl]carbenium chloride (CI 42595; Basic Blue No. 7); di-(4-(dimethylamino)phenyl)-(4-(methyl-phenylamino)naphthalene-1-yl)carbenium chloride (CI42563; Basic Blue No. 8); 3,7-di(methylamino) phenothiazine-5-ium chloride (CI 52015; Basic Blue No. 9); di[4-(dimethylamino)phenyl]-[4-(phenylamino)naphthyl]-carbenium chloride (CI 44045; Basic Blue No. 26); 2-[(4-(ethyl(2-hydroxyethyl)amino)phenyl)azo]-6-methoxy-3-methyl-benzothiazolium methyl sulfate (CI 1154; Basic Blue No. 41); 8-amino-2-bromo-5-hydroxy-4-imino-6-[(3-(trimethylammonio)phenyl-amino]-1(4H)-naphthalenone chloride (CI 56059; Basic Blue No. 99); bis[4-(dimethylamino)phenyl][4-(methylamino)phenyl]-carbenium chloride (CI 42535; Basic Violet No. 1); tri-(4-amino-3-methylphenyl)carbenium chloride (CI42520; Basic Violet No. 2); tris[4-(dimethylamino)phenyl]carbenium chloride (CI42555; Basic Violet No. 3); 2-[3,6-(diethylamino)dibenzo-pyranium-9-yl]-benzoic acid chloride (CI 45170; Basic Violet No. 10); di(4-aminophenyl)(4-amino-3-methyl-phenyl)carbenium chloride (CI 42510; Basic Violet No. 14); 1,3-bis[(2,4-diamino-5-methylphenyl) azo]-3-methylbenzene (CI 21010; Basic Brown No. 4); 1-[(4-aminophenyl)azo]-7-(trimethylammonio)-2-naphthol chloride (CI 12250; Basic Brown No. 16); 1-[(4-amino-2-nitrophenyl)azo]-7-(trimethylammonio)-2-naphthol chloride (Basic Brown No. 17); 1-[(4-amino-3-nitrophenyl)azo]-7-(trimethylammonio)-2-naphthol chloride (CI 12251; Basic Brown No. 17); 3,7-diamino-2,8-dimethyl-5-phenylphenazinium chloride (CI 50240; Basic Red No. 2); 1,4-dimethyl-5-[(4-(dimethylamino)-phenyl)azo]-1,2,4-triazolium chloride (CI 11055; Basic Red No. 22); 2-hydroxy-1-[(2-methoxyphenyl)azo]-7-(trimethylammonio)-naphthalene chloride (CI 12245; Basic Red No. 76); 2-[2-((2,4-dimethoxyphenyl)amino)-ethenyl]-1,3,3,-trimethyl-3H-indole-1-ium chloride (CI 48055; Basic Yellow No. 11); 3-methyl-1-phenyl-4-[(3-trimethylammonio)phenyl)azo]-pyrazole-5-one chloride (CI 12719; Basic Yellow No. 57); bis[4-(diethylamino)-phenyl]-phenylcarbenium hydrogen sulfate (1:1) (CI 42040; Basic Green No. 1); di(4-(dimethylamino)phenyl)-phenylmethanol (CI42000; Basic Green No. 4); di(4-(dimethylamino)phenyl)iminomethane hydrochloride (CI41000; Basic Yellow No. 2); 4-[(4-aminophenyl)azo]-1-[di(2-hydroxyethyl)amino]-3-methylbenzene (HC Yellow No. 7) or 2,6-diamino-3-((pyridine-3-yl)azo)-pyridine.

The substantive dyes, named above, may be contained in a total amount of 0.01 to 4% by weight, the total amount of dyes in the inventive dying agent preferably being about 0.01 to 10% by weight and especially 0.1 to 5% by weight.

The inventive dyeing agent furthermore may contain all additives, known and customary for such preparations, such as perfume oils, complexing agents, waxes, preservatives, thickeners, alginates, guar gum, hair-care substances such as cationic polymers or lanolin derivatives, or anionic, nonionic, amphoteric or cationic surface active substances. Preferably, amphoteric or nonionic surface active substances, such as betaine surfactants, propionates and glycinates, such as coconut oil amphoglycinates, ethoxylated surfactants with 1 to 1000 ethylene oxide units, preferably with 1 to 300 ethylene oxide units, such as ethoxylated glycerides, such as caster oil ethoxylated with 25 ethylene oxide units, polyglycolamides, ethoxylated alcohol and ethoxylated fatty alcohols (fatty alcohol ethoxylates) and ethoxylated fatty acid sugar esters, especially ethoxylated esters of fatty acids and sorbitol. The aforementioned components are used in amounts customary for such purposes. For example, the surface-active substances are used in concentrations of 0.1 to 30% by weight and the care materials in amounts of 0.1 to 5% by weight.

Aside from water, the inventive dyeing agent may also contain organic solvents, such as aliphatic or aromatic alcohols, such as ethanol, isopropanol, 1,2-propanediol, 1-methoxypropane-2-ol, 1-ethoxy-propane-2-ol, diethylene glycol monomethyl ether or diethylene glycol monoethyl ether, dipropylene glycol monomethyl ether, dipropylene glycol monoethyl ether, benzyl alcohol, benzyloxyethanol, phenylethyl alcohol, phenoxyethanol, cinnamic alcohol and glycol ether, especially ethanol. As a rule, the water content is about 25 to 95% by weight and preferably 30 to 85% by weight, whereas the organic solvent or organic solvent mixture content is about 5 to 30% by weight.

Especially if it is a hair dye, the inventive dyeing agent may be in the form of an aqueous or aqueous, alcoholic solution, a cream, a gel, an emulsion or an aerosol foam. The hair dyeing agent may be produced in the form of a one-component preparation as well as in the form of multi-component preparation, such as a two-component preparation, for which the dye derivative of formula (I) is packaged separately from the remaining components and the ready-for-use hair dyeing agent is prepared immediately before use by mixing the two components.

The inventive dyeing agent has a pH of about 2 to 10 and preferably of about 5 to 10 and especially a neutral to basic pH of about 7 to 10. Organic, as well as inorganic acids or bases, are suitable for adjusting the inventive pH.

In particular, the following may be mentioned as suitable acids: α-hydroxycarboxylic acids, such as glycolic acid, lactic acid, tartaric acid, citric acid or malic acid: ascorbic acid; gluconic acid lactone; acetic acid; hydrochloric acid or phosphorous acid, as well as mixtures of these acids.

In particular, the following may be mentioned as suitable bases: sodium carbonate, sodium hydrogen carbonate, potassium carbonate, potassium hydrogen carbonate, sodium phosphate, borax ($Na_2B_4O_7 \times 10H_2O$), disodium hydrogen phosphate, alkanolamines, such as monoethanolamine or triethanolamine, ammonium hydroxide, aminomethylpropanol and sodium hydroxide.

The inventive dyeing agents usually are used by applying on the hair an amount of hair dyeing agent, which is sufficient for dyeing the hair and varies from about 30 to 120 grams, depending on the length of the hair, and allowing the hair dyeing agent to act for about 1 to 60 minutes and preferably 5 to 30 minutes at a temperature of 15° to 45° C. Subsequently, the hair is rinsed thoroughly with water, optionally shampooed and finally dried.

For cosmetic agents, the dyeing agent described above may furthermore contain conventional, natural or synthetic polymers or modified polymers of natural origin, by means of which a strengthening of the hair is achieved simultaneously with the dyeing. Such agents generally are referred to as shade or color setting agents.

Of the synthetic polymers known for this purpose in cosmetics, the following are mentioned as examples: polyvinylpyrrolidone, polyvinyl acetate, polyvinyl alcohol or polyacrylic compounds, such as polyacrylic acid or polymethacrylic acid, basic polymers of esters of polyacrylic acid, polymethacrylic acid and amino alcohols, such as their salts or quaternization products, polyacrylonitrile, polyvinyl acetates and copolymers of such compounds, such as polyvinylpyrrolidone vinyl acetate; on the other hand, as natural polymers or modified natural polymers, chitosan (de-acetylated chitin) or chitosan derivatives may, for example, be used.

The aforementioned polymers may be contained in the inventive agent in amounts, customary for such agents, especially in an amount of about 1 to 5% by weight. The pH of the inventive shade or color fortifiers preferably is about 6 to 9.

The hair-dyeing agent with additional setting properties is applied in the usual and known manner by moistening the hair with the fortifier, fixing the hair for styling and subsequently drying.

The inventive dyeing agent makes possible an outstanding, uniform, and extremely permanent coloration of keratin fiber (such as human hair, wool or fur) without any staining of the skin or scalp worth mentioning. The coloration survives 5 or more washings of the hair without a noticeable fading of the hair color.

The following examples are to explain the object of the invention in greater detail, without limiting it to these examples.

EXAMPLES

Example 1

Synthesis of 2,5-bis(4-trimethylammonium-butyl)-3,6-diphenyl-pyrrolo[3,4-c]pyrrole-1,4-dione dibromide Step 1

Synthesis of 2,5-bis(4-bromobutyl)-3,6-diphenyl-pyrrolo[3,4-c]pyrrole-1,4-dione 2,5-Dihydro-3,6-diphenyl-pyrrolo[3,4-c]pyrrole-1,4-dione (5 g, 17.3 mmoles) (formula (II) with Q1=Q2=phenyl) is suspended in 55 ml of N-methylpyrrolidone and cooled with stirring to 0° C. At this temperature, 1.73 g (43.2 mmoles) of sodium hydride (a 60% suspension in oil) are added and the mixture is subsequently stirred slowly at first and then vigorously. The mixture is then stirred for 1.5 hours at room temperature and cooled once again to 0° C. The reaction mixture is treated first with a spatula tip of potassium iodide and then dropwise with 29.88 g (138 mmoles) of dibromobutane in 80 mL of N-methylpyrrolidone. Subsequently, the reaction mixture is stirred overnight at room temperature and then poured onto ice. The precipitated orange-colored product is filtered, washed with hexane and water and subsequently dried.

Yield: 7.48 g (77% of the theoretical), red powder $^1$H-NMR (DMSO/300 MHz): 7.82 (d, J=7 Hz, 4H aromat.), 7.58 (m, 6H aromat.), 3.73 (t, J=7, 1 Hz, 4H, $CH_2$—N), 3.40 (t, J=6.5 Hz, 4H, $CH_2$—Br), 1.65 (m, 4H, $CH_2$), 1.54 (m, 4H, $CH_2$).

Step 2

Synthesis of 2,5-bis(4-trimethylammonium-butyl)-3,6-diphenyl-pyrrolo[3,4-c]pyrrole-1,4-dione dibromide 2,5-Bis(4-bromobutyl)-3,6-diphenyl-pyrrolo(3,4-c]pyrrole-1,4-dione (2 g, 3.6 mmoles) from step 1 are dissolved in 55 mL of a 10:1 mixture of toluene and ethanol and treated with 8.5 mL (36 mmoles) of a 33% ethanolic solution of trimethylamine. The reaction mixture is heated for about 5 hours at 65° C. and then cooled. The precipitated product is filtered off, washed with toluene and ethyl acetate and subsequently dried.

Yield: 2.17 g (89% of the theoretical), red powder $^1$H-NMR (DMSO/300 MHz): 7.83 (m, 4H aromat.), 7.59 (m, 6H aromat.), 3.73 (m, 4H, $CH_2$—N), 3.21 (m, 4H, $CH_2$—N$^+$), 3.0 (s, 18H, $CH_3$), 1.58 (m, 4H, $CH_2$) 1.46 (m, 4H, $CH_2$).

MS (ESI): 258 (M$^{2+}$/2).

The crude product, so obtained, can be used directly in the inventive hair-dyeing agent without further purification.

Example 2

Synthesis of 2,5-bis(4-trimethylammonium-butyl)-3,6-bis[4-(dimethylamino)phenyl]-pyrrolo[3,4-c]pyrrole-1,4-dione dibromide Step 1

Synthesis of 2,5-bis(4-bromobutyl)-3,6-bis[4-(dimethylamino)-phenyl]-pyrrolo[3,4-c]pyrrole-1,4-dione 3,6-Bis(4-dimethylamino)phenyl]-2.5-dihydro-pyrrolo[3,4-c]pyrrole-1,4-dione (5 g, 13.4 mmoles) (formula (II) with Q1=Q2=$C_6H_4$—N(CH$_3$)$_2$), is suspended in 150 mL of N-methylpyrrolidone and cooled to 0° C. At this temperature, 1.46 g (33.5 mmoles) of sodium hydride (a 60% suspension in oil is added and the mixture is subsequently stirred, slowly at first and then vigorously. After being stirred for 1.5 hours at room temperature, the reaction mixture is cooled once again to 0° C. and treated with a spatula tip of potassium iodide. While stirring, 23.1 g (106.8 mmoles) of dibromobutane are then added dropwise and the reaction mixture is stirred overnight at room temperature. Subsequently, the reaction mixture is poured into water and the mixture obtained is stirred 2 hours at 80° C. The precipitated violet product is filtered off, washed with hexane and ethanol and then dried.

Yield: 5.9 g (69% of the theoretical), violet powder $^1$H-NMR (DMSO/300 MHz: 7.83 (d, J=9.0 Hz, 4H aromat.), 6.82 (d, J=9.0 Hz, 4H aromat.), 3.81 (m, 4H, $CH_2$—N), 3.47 (m, 4H, $CH_2$—Br), 3.03 (s, 12H, $CH_3$—N), 1.72 (m, 4H, $CH_2$), 1.65 (m, 4H, $CH_2$).

Step 2

Synthesis of 2,5-bis(4-trimethylammonium-butyl)-3,6-bis[4-(dimethylamino)phenyl]-pyrrolo[3,4-c]pyrrole-1,4-dione dibromide 5-Bis(4-bromobutyl)-3,6-bis[4-(dimethylamino)-phenyl]-pyrrolo[3,4-c]pyrrole-1,4-dione (4 g, 6.2 mmoles) from step 1 is dissolved in 100 mL of toluene and treated with 14.8 mL (62 mmoles) of a 33% ethanolic solution of trimethylamine. The reaction mixture is stirred for 5.5 hours at 65° C. and then cooled. The precipitated product is filtered off, washed with toluene, ethanol and acetone and subsequently dried.

Yield: 4.5 g (95% of the theoretical), violet powder $^1$H-NMR (DMSO/300 MHz): 7.82 (d, J=8.9 Hz, 4H aromat.), 6.82 (d, J=8.9 Hz, 4H aromat.), 3.80 (m, 4H, $CH_2$—N), 3.30 (m, 4H, $CH_2$—N$^+$), 3.04 (s, 12H, $CH_3$—N), 3.0 (s, 18H, $CH_3$—N$^+$), 1.65 (m, 4H, $CH_2$), 1.54 (m, 4H, $CH_2$).

MS (ESI): 301 (M$^{2+}$/2).

The crude product, so obtained can be used directly in the inventive hair-dyeing agent without further purification Example 3

Synthesis of 2,5-bis[4-[4-(dimethylamino)pyridinium]-butyl]-3,6-diphenyl-pyrrolo[3,4-c]pyrrole-1,4-dione dibromide 2,5-Bis(4-bromobutyl)-3,6-diphenyl-pyrrolo[3,4-c]pyrrole-1,4-dione (1 g, 1.8 mmoles) from step 1 of example 1 is dissolved in 30 mL of toluene and treated with 2.2 g (18 mmoles) of 4-(dimethylamino)-pyridine. The reaction mixture is stirred for 7.5 hours at 55° C. and then cooled. The precipitated product is filtered off, washed with toluene, ethanol and subsequently dried.

Yield: 0.76 g (53% of the theoretical), orange powder $^1$H-NMR (DMSO/300 MHz): 8.21 (d, J=7.3 Hz, 4H pyridinium), 7.79 (m, 4H aromat.), 7.59 (m, 6H aromat.), 6.98 (d, J=7.3 Hz, 4H pyridinium), 4.09 (m, 4H, $CH_2$—N$^+$), 3.75 (m, 4H, $CH_2$—N), 3.20 (s, 12H, N—$CH_3$), 1.65 (m, 4H, $CH_2$), 1.35 (m, 4H, $CH_2$).

MS (ESI): 321 (M$^{2+}$/2).

The crude product, so obtained, can be used directly in the inventive hair-dyeing agent without further purification Example 4

Synthesis of 2,5-bis[4-[N-(methylimidazolium)butyl]]-3,6-diphenyl-pyrrolo[3,4-c]pyrrole-1,4-dione dibromide 2,5-Bis(4-bromobutyl)-3,6-diphenyl-pyrrolo[3,4-c]pyrrole-1.4-dione (1 g, 1.8 mmoles) from step 1 of example 1 is dissolved in 33 mL of a 10:1 mixture of toluene and ethanol and treated with 1.47 g (18 mmoles) of N-methylimidazole. The reaction mixture is stirred for 3 days at 110° C. and then cooled. The precipitated product is filtered off, washed with toluene and ethanol and subsequently dried.

Yield: 1.2 g (93% of the theoretical), orange powder $^1$H-NMR (DMSO/300 MHz): 9.05 (s, 2H, H(2) imidazolium), 7.82 (m, 4H aromat.), 7.69 (m, 4H, H(4) and H(5) imidazolium), 7.62 (m, 6H aromat.), 4.10 (t, 4H, $CH_2$—N$^+$), 3.82 (s, 6H, N—$CH_3$), 3.75 (t, 4H, $CH_2$—N), 1.68 (m, 4H, $CH_2$), 1.40 (m, 4H, $CH_2$).

MS (ESI): 281 (M$^{2+}$/2).

The crude product, so obtained, can be used directly in the inventive hair-dyeing agent without further purification.

Examples 5 to 8

Hair Dyeing Agent

Dyeing Solution

| | |
|---|---|
| 2.5 mmoles | dye of formula (I) |
| 5.0 g | ethanol |
| 2.0 g | decylpolyglucose |
| 0.2 g | disodium salt of ethylenediaminotetraacetic acid hydrate |
| ad 100.0 g | water, fully desalinated |

The pH of the dyeing solution is adjusted to a value of 7 to 10 by the addition of ammonia.

The hair is dyed by applying an amount of the dyeing agent, sufficient for the dyeing, on the hair. After a period of action of 30 minutes at 40° C., the hair is rinsed with lukewarm water, shampooed, rinsed once again with water and dried. The dyeing results are summarized in the following Table 1.

TABLE 1

| Example No./ Dye of Formula (I) | Dyeing | L*a*b- Color Values | Fluorescence Upon Stimulation λ = 366 nm |
|---|---|---|---|
| 5 2,5-bis(4-trimethylammonium-butyl)-3,6-diphenyl-pyrrolo[3,4-c]pyrrole-1,4-dione dibromide | yellow-orange | L = 71.08 a = 20.26 b = 89.58 | fluorescing yellow |
| 6 2,5-bis(4-trimethylammonium-butyl)-3,6-bis[4-(dimethylamino)phenyl]-pyrrolo[3,4-c]pyrrole-1,4-dione dibromide | violet | L = 24.88 a = 32.85 b = −10.53 | fluorescing red |
| 7 2,5-bis[4-(dimethylamino)-pyridinium]butyl]-3,6-diphenyl-pyrrolo-[3,4-c]pyrrole-1,4-dione dibromide | yellow-orange | L = 76.05 a = 15.95 b = 97.02 | fluorescing yellow |
| 8 2,5-bis[4-[N-(methylimidazolium)-butyl]]-3,6-diphenyl-pyrrolo-[3,4-c]pyrrole-1,4-dione dibromide | yellow-orange | L = 76.58 a = 15.80 b = 95.34 | fluorescing yellow |

Examples 9 to 16

Hair Dyeing Agent

Dye Solution

| X mmoles | Dye of formula (I) (amount as given in Table 2) |
| Y mmoles | direct dyes (type and amount as in Table 2) |
| 5.0 g | ethanol |
| 2.0 g | decylpolyglucose |
| 0.2 g | disodium salt of ethylenediaminotetraacetic acid hydrate |
| ad 100.0 g | water, fully desalinated |

The pH of the dye solution is adjusted to a value of 7 to 10 by the addition of ammonia.

The hair is dyed by applying an amount of the dyeing agent, sufficient for the dyeing, on the hair. After a period of action of 30 minutes at 40° C., the hair is rinsed with lukewarm water, shampooed, rinsed once again with water and dried. The dyeing results are summarized in the following Table 2

TABLE 2

| Example No./ Dye of Formula (I) | Dyeing | L*a*b- Color Values |
|---|---|---|
| 9 2,5-bis(4-trimethylammonium-butyl)-3,6-diphenyl-pyrrolo[3,4-c]pyrrole-1,4-dione dibromide (1.25 mmoles) and 3-methyl-1-phenyl-4-[(3-(trimethylammonium)phenyl)azo]-pyrazole-5-one chloride (Basic Yellow No. 57) (1.25 mmoles) | Bright golden | L = 69.80 a = 16.71 b = 82.65 |
| 10 2,5-bis(4-trimethylammonium-butyl)-3,6-diphenyl-pyrrolo[3,4-c]pyrrole-1,4-dione dibromide (1.25 mmoles) and 2-hydroxy-1-[(2-methoxyphenyl)azo]-7-(trimethylammonium)-naphthalene-chloride (Basic Red No. 76) (1.25 mmoles) | Bright orange | L = 47.75 a = 48.66 b = 48.18 |
| 11 2,5-bis(4-trimethylammonium-butyl)-3,6-diphenyl-pyrrolo[3,4-c]pyrrole-1,4-dione dibromide (1.25 mmoles) and 1-[(4-aminophenyl)azo]-7-(trimethylammonium)-2-naphthol-chloride (Basic Brown No. 16) (1.25 mmoles) | Bright mahogany | L = 23.10 a = 19.84 b = 10.61 |
| 12 2,5-bis(4-trimethylammonium-butyl)-3,6-bis[4-(dimethylamino)phenyl]-pyrrolo[3,4-c]pyrrole-1,4-dione dibromide (1.25 mmoles) and 2-hydroxy-1-[(2-methoxyphenyl)azo]-7-(trimethylammonio)-naphthaline-chloride (Basic Red No. 76) (1.25 mmoles) | Bright cherry red | L = 30.01 a = 35.74 b = 8.97 |
| 13 2,5-bis(4-trimethylammonium-butyl)-3,6-bis[4-(dimethylamino)phenyl]-pyrrolo[3,4-c]pyrrole-1,4-dione dibromide (1.25 mmoles) and 8-amino-2-bromo-5-hydroxy-4-imino-6-[(3-(trimethylammonium)phenyl)-amino]-1-(4H)-naphthalenone-chloride (Basic Blue No. 99) (1.25 mmoles) | Bright blue | L = 21.81 a = 8.65 b = −12.82 |
| 14 2,5-bis(4-trimethylammonium-butyl)-3,6-bis[4-(dimethylamino)phenyl]-pyrrolo[3,4-c]pyrrole-1,4-dione dibromide (1.25 mmoles) and 1-[(4-aminophenyl)azo]-7-(trimethylammonium)-2-naphthol-chloride (Basic Brown No. 16) (1.25 mmoles) | Bright brownish red | L = 20.06 a = 17.53 b = 6.47 |
| 15 2,5-bis(4-trimethylammonium-butyl)-3,6-diphenyl-pyrrolo[3,4-c]pyrrole-1,4-dione dibromide (0.41 mmoles) and 3-methyl-1-phenyl-4-[(3-(trimethyl-ammonium)phenyl)azo]-pyrazole-5-one-chloride (Basic Yellow No. 57) (0.41 mmoles); 2-hydroxy-1-[(2-methoxyphenyl)azo]-7-(trimethylammonium)-naphthalene-chloride (Basic Red No. 76) (0.41 mmoles); 1-[(4-aminophenyl)azo]-7-(trimethyl-ammonium-2-naphthol-chloride (Basic Brown No. 16) (0.41 mmoles); 1-[(4-amino-3-nitrophenyl)azo]-7-(trimethyl-ammonium)-2-naphthol-chloride (Basic Brown No. 17) (0.41 mmoles); 8-amino-2-bromo-5-hydroxy-4-imino-6-[(3-(trimethylammonium)phenyl)-amino]-1-(4H)-naphthalenone-chloride (Basic Blue No. 99) (0.41 mmoles) | Bright mahogany | L = 25.18 a = 13.52 b = 11.23 |
| 16 2,5-bis(4-trimethylammonium-butyl)-3,6-diphenyl-pyrrolo[3,4-c]pyrrole-1,4-dione dibromide (0.41 mmoles) and 3-methyl-1-phenyl-4-[(3-(trimethyl-ammonium)phenyl)azo]-pyrazole-5-one-chloride (Basic Yellow No. 57) (0.41 mmoles); 2-hydroxy-1-[(2-methoxyphenyl)azo]-7-(trimethylammonium)-naphthalene-chloride (Basic Red No. 76) (0.41 mmoles); 1-[(4-aminophenyl)azo]-7-(trimethyl-ammonium)-2-naphthol-chloride (Basic Brown No. 16) (0.41 mmoles); | Bright brownish red | L = 23.39 a = 12.93 b = 8.98 |

TABLE 2-continued

| Example No./ Dye of Formula (I) | Dyeing | L*a*b- Color Values |
|---|---|---|
| 1-[(4-amino-3-nitrophenyl)azo]-7-(trimethyl-ammonium)-2-naphthol-chloride (Basic Brown No. 17) (0.41 mmoles); 8-amino-2-bromo-5-hydroxy-4-imino-6-[(3-(trimethylammonium)phenyl)-amino]-1(4H)-naphthalenone-chloride (Basic Blue No. 99) (0.41 mmoles) | | |

The L*a*b* color values were measured with a Minolta colorimeter, Type Chromameter II. The L value represents the brightness (that is, the lower the L value, the greater is the color intensity), while the a value is a measure of the red portion (that is, the greater the a value, the greater is the proportion of red). The b value is a measure of the blue portion of the color in the sense that a more negative value of b indicates a greater proportion of blue.

Unless stated otherwise, all percentages, given in the Application, are percentages by weight.

What is claimed is:

1. A cationic diketopyrrolopyrrole of the general formula (I)

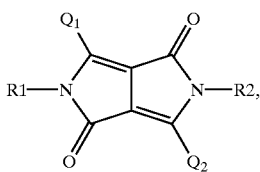

wherein, independently of one another, $Q_1$ and $Q_2$ represent an optionally substituted, aromatic, isocyclic or heterocyclic group with 5 to 14 atoms in the ring, the heterocyclic group containing at least one oxygen, nitrogen or sulfur atom, and the R1 and R2 groups, independently of one another, represent hydrogen or a Y—B$^+$A$^-$ group, with the proviso that at least one of the R1 and R2 groups is not hydrogen; B$^+$ is an aromatic, aliphatic, alicyclic, aromatic heterocyclic or non-aromatic heterocyclic, quaternary ammonium group or a quaternary phosphonium group; Y is an optionally substituted linear or branched $C_1$ to $C_6$ alkylene group and A$^-$ is an anion.

2. The diketopyrrolopyrrole of claim 1, wherein, in formula (I), B$^+$ represents (i) an aromatic, heterocyclic quaternary ammonium compound; (ii) a non-aromatic, heterocyclic quaternary ammonium compound; (iii) a quaternary alkylammonium compound or arylammonium compound, arylalkylammonium compound of formula NR$^5$R$^6$R$^7$, in which R$^5$, R$^6$ and R$^7$ independently of one another are a benzyl group, a phenyl group or a $C_1$ to $C_6$ alkyl group, the aforementioned alkyl groups being unsubstituted or substituted with one or more hydroxy groups or amino groups; or (iv) a quaternary phosphonium compound.

3. The diketopyrrolopyrrole of claims 1, wherein, in formula (I), Y represents a —CH$_2$— group, a —CH$_2$—CH$_2$— group, a —CH$_2$—CH$_2$—CH$_2$— group, a —CH$_2$—CH$_2$—CH$_2$—CH$_2$— group or a linear or branched $C_2$ to $C_6$ alkylene group, substituted with one or more alkyl groups, hydroxy groups, amino groups, acyl groups or quaternary ammonium groups.

4. The diketopyrrolopyrrole of claim 1, wherein, in formula (I), the anion A$^-$ is selected from iodide, chloride, bromide, sulfate, phosphate, hydrogen phosphate, oxalate, carbonate, hydrogen carbonate, formate, acetate, citrate, tartrate, malonate and pyruvate.

5. A process for the synthesis of diketopyrrolopyrroles of formula (I) of claim 1, for which a compound of formula (II) is reacted with the appropriate alkyl dihalide in the presence of a base in an aprotic polar solvent and the halide obtained is subsequently reacted with a tertiary amine or a tertiary phosphine

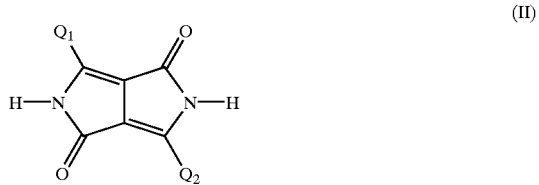

wherein $Q_1$ and $Q_2$ are as defined as in claim 1.

6. The process for the synthesis of the diketopyrrolopyrroles of formula (I) of claim 1, for which a compound of the general formula (II)

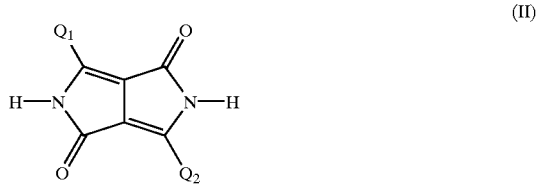

is reacted with cationic chain X—Y—B$^+$A$^-$, wherein $Q_1$, $Q_2$, X, —Y, B$^+$ and A$^-$ are as defined as in claim 1.

7. An dye composition for dyeing keratin fibers, wherein the composition contains at least one diketopyrrolopyrrole compound of formula (I) as defined in claim 1.

8. The dye composition of claim 7, wherein the diketopyrrolopyrrole compound of formula (I) is selected from the group consisting of 2,5-bis-(4-trimethylammoniumbutyl)-3,6-diphenyl-pyrrolo[3,4-c]pyrrole-1,4-dione dibromide, 2,5-bis(4-trimethylammonium-butyl)-3,6-diphenyl-pyrrolo[3,4-c]pyrrole-1,4-dione dichloride, 2,5-bis(4-trimethylammonium-butyl)-3,6-bis[4-dimethylamino)phenyl]-pyrrolo[3,4-c]-1,4-dione dibromide, 2,5-bis(4-trimethylammonium-butyl)-3,6-bis[4-(dimethylamino)phenyl]-pyrrolo[3,4-c]pyrrole-1,4-dione dichloride, 2,5-bis[4-[4-(dimethylamino)pyridinium]butyl]-3,6-diphenyl-pyrrolo[3,4-c]pyrrole-1,4-dione dibromide; 2,5-bis[4-[4-(dimethylamino)pyridinium]-butyl]-3,6-diphenyl-pyrrolo-[3,4-c]pyrrole-1,4-dione dichloride; 2,5-bis[4-[N-(methylimidazolium)butyl]]-3,6-diphenyl-pyrrolo[3,4-c]pyrrole-1,4-dione dibromide and 2,5-bis[4-[N-(methylimidazolium)butyl]]-3,6-diphenyl-pyrrolo[3,4-c]pyrrole-1,4-dione dichloride.

9. The dye composition of claim 7, wherein the diketopyrrolopyrrole compound of formula (I) is contained in an amount of 0.01 to 10% by weight.

10. The dye composition of claim 7, wherein it contains additionally at least one further direct dye from the group, consisting of plant dyes, nitro dyes, azo dyes, anthraquinone dyes and triphenylmethane dyes.

11. A method for dyeing hair comprising applying a dye composition as defined in claim 7 to the hair in an amount sufficient for the dyeing of said hair.

* * * * *